US012558313B2

(12) United States Patent
Maes et al.

(10) Patent No.: US 12,558,313 B2
(45) Date of Patent: Feb. 24, 2026

(54) GOLF BALL-LIKE MICROPARTICLES FOR USE IN THE TREATMENT AND PREVENTION OF PULMONARY DISEASES

(71) Applicant: AQUILON PHARMACEUTICALS SA, Vise (BE)

(72) Inventors: Paul Maes, Vise (BE); Didier Cataldo, Olne (BE); William Bigazzi, Donceel (BE); Brigitte Evrard, Embourg (BE)

(73) Assignee: AQUILON PHARMACEUTICALS, Vise (BE)

( * ) Notice: Subject to any disclaimer, the term of this patent is extended or adjusted under 35 U.S.C. 154(b) by 611 days.

(21) Appl. No.: 17/641,416

(22) PCT Filed: Sep. 10, 2020

(86) PCT No.: PCT/EP2020/075416
§ 371 (c)(1),
(2) Date: Mar. 8, 2022

(87) PCT Pub. No.: WO2021/048322
PCT Pub. Date: Mar. 18, 2021

(65) Prior Publication Data
US 2023/0218515 A1    Jul. 13, 2023

(30) Foreign Application Priority Data
Sep. 10, 2019    (BE) ................................. 2019/5603

(51) Int. Cl.
| A61K 9/00 | (2006.01) |
| A61K 9/16 | (2006.01) |
| A61K 31/167 | (2006.01) |
| A61K 31/58 | (2006.01) |

(52) U.S. Cl.
CPC .......... *A61K 9/0075* (2013.01); *A61K 9/1617* (2013.01); *A61K 9/1652* (2013.01); *A61K 9/1682* (2013.01); *A61K 31/167* (2013.01); *A61K 31/58* (2013.01)

(58) Field of Classification Search
CPC .. A61K 9/0075; A61K 9/1617; A61K 9/1652; A61K 9/1682; A61K 31/167; A61K 31/58; A61K 31/198; A61K 45/06; A61K 31/573; A61K 31/137; A61K 47/40; A61P 11/00; A61P 11/08
See application file for complete search history.

(56) References Cited

U.S. PATENT DOCUMENTS

| 9,993,487 B2 * | 6/2018 | Cataldo ................... A61P 11/00 |
| 2010/0092453 A1 | 4/2010 | Healy et al. |
| 2017/0312258 A1 | 11/2017 | Sung et al. |

FOREIGN PATENT DOCUMENTS

| AU | 2006200277 B2 | 2/2006 |
| CN | 106924193 A | 7/2017 |
| EP | 1906919 | 4/2008 |
| EP | 1799231 B1 | 2/2010 |
| EP | 2923792 A1 | 9/2015 |
| EP | 3151836 A2 | 4/2017 |
| WO | WO02/28377 A1 | 4/2002 |
| WO | WO2004052334 A2 | 6/2004 |
| WO | WO2007011989 A2 | 1/2007 |
| WO | WO 2013082111 A2 | 6/2012 |
| WO | WO2015144938 A2 | 10/2015 |
| WO | WO20151445938 A3 | 3/2016 |

OTHER PUBLICATIONS

Hoppentocht et. al. Technological and practical challenges of dry powder inhalers and formulations. Advanced Drug Delivery Reviews 75 (2014) 18-31. (Year: 2014).*
Kim et. al. Golf ball-shaped PLGA microparticles with internal pores fabricated by simple O/W emulsion. Chem. Commun., 2010, 46, 7433-7435. (Year: 2010).*
Okubo et. al. Thermodynamic aspects of the heterogeneous structure of "golf-ball-like" polymer particles. Colloid Polym Sci 277: 1005±1008 (1999). (Year: 1999).*
Chowdhury et. al. A study of dimple characteristics on golf ball drag. Procedia Engineering 147 ( 2016 ) 87-91. (Year: 2016).*
Day et. al. Quantifying the hygroscopic properties of cyclodextrin containing aerosol for drug delivery to the lungs. Phys.Chem.Chem. Phys., 2020, 22, 11327 (Year: 2020).*
Miyamoto et. al. Simple Method to Measure the Aerodynamic Size Distribution of Porous Particles Generated on Lyophilizate for Dry Powder Inhalation. Pharmaceutics 2020, 12, 976. (Year: 2020).*
Sano et. al. "Inhaled budesonide for the treatment of acute wheezing and dyspnea in children up to 24 months old receiving intravenous hydrocortisone." J Allergy Clin Immunol vol. 105, No. 4, (2000) 699-702. (Year: 2000).*
Ziaee et. al. "Spray drying of pharmaceuticals and biopharmaceuticals: Critical parameters and experimental process optimization approaches" European Journal of Pharmaceutical Sciences 127 (2019) 300-318 (Year: 2019).*
Dufour "Interest of cyclodextrins in spray-dried microparticles formulation for sustained pulmonary delivery of budesonide" International Journal of Pharmaceutics 495 (2015) 869-878. (Year: 2015).*
Kim "Golf ball-shaped PLGA microparticles with internal pores fabricated by simple O/W emulsion" Chem. Commun., 2010, 46, 7433-7435. (Year: 2010).*
Cui "Moisture-Resistant Co-Spray-Dried Netilmicin with L-Leucine as Dry Powder Inhalation for the Treatment of Respiratory Infections" Pharmaceutics 2018, 10, 252. (Year: 2018).*
Yang "Preparation and In Vitro Aerosol Performance of Spray-Dried Shuang-Huang-Lian Corrugated Particles in Carrier-Based Dry Powder Inhalers" AAPS PharmSciTech, vol. 13, No. 3, Sep. 2012. (Year: 2012).*

(Continued)

*Primary Examiner* — Ali Soroushi
*Assistant Examiner* — Rajan Pragani
(74) *Attorney, Agent, or Firm* — Peter Manso, Esq.; Lewis Brisbois; Bisgaard & Smith LLP

(57) ABSTRACT

The present invention relates to a golf ball-like microparticles obtained by atomization of nanosuspensions of nanoparticles or solutions for dry powder inhalers for use in the treatment and prevention of pulmonary diseases.

16 Claims, 14 Drawing Sheets

(56) References Cited

OTHER PUBLICATIONS

Okubo "Thermodynamic aspects of the heterogeneous structure of "golf-ball-like" polymer particles" Colloid Polym Sci 277:1005± 1008 (1999). (Year: 1999).*

International Search Report dated Nov. 26, 2020 issued in PCT/ EP2020/075416.

E. Lintingre, F. Lequeux, Laurence Talini, N. Tsapis. Control of particle morphology in the spray drying of colloidal suspensions. Soft Matter, Royal Society of Chemistry, 2016, 12 (36), pp. 7435- 7444 10.1039/C6SM01314, HAL ID: hal-01368558 https://hal. sorbonne-universite.fr/hal-01368558 submitted on Sep. 19, 2016.

Zhao, Z., et al. (2018) "Low density, good flowability cyclodextrin-raffinose binary carrier for dry powder inhaler: anti-hygroscopicity and aerosolization performance enhancement," Expert Opinion on Drug Delivery, DOI: 10.1080/17425247.2018.1450865.

DuFour, Gilles et al: "Interest of cyclodextrins in spray-dried microparticles formulation for sustained pulmonary delivery of budesonide", International Journal of Pharmaceutics, Els Ev I Er, NL, vol. 495, No. 2, Sep. 26, 2015 (Sep. 26, 2015), pp. 869-878, XPO29292206, ISSN: 03 78-5173, DOI: 1.10162, J IJPHARM. 2015.09.052.

Newman PhD, Stephen P., Fine Particle Fraction: The Good and the Bad, Journal of Aerosol Medicine and Pulmonary Drug Delivery, vol. 35 No. 1, 2022, pp. 2-10 DOI: 10.1089/jamp.2021.29056.spn.

Lechanteur, Et. Al., Influence of Composition and Spray-Drying Process Parameters on Carrier-Free DPI Properties and Behaviors in the Lung: A review, Pharmaceutics 2020, 12, 55; doi: 10.3390/ pharmaceutics 12010055.

* cited by examiner

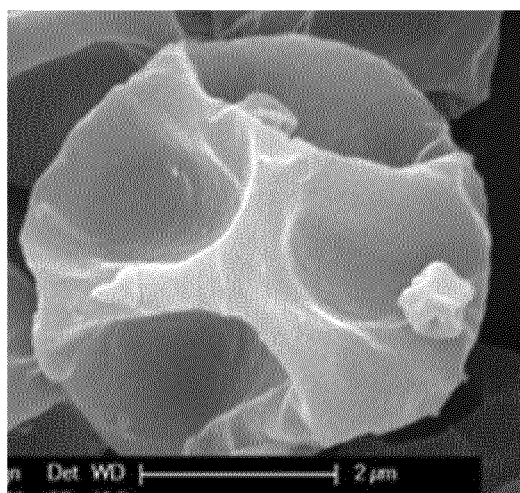
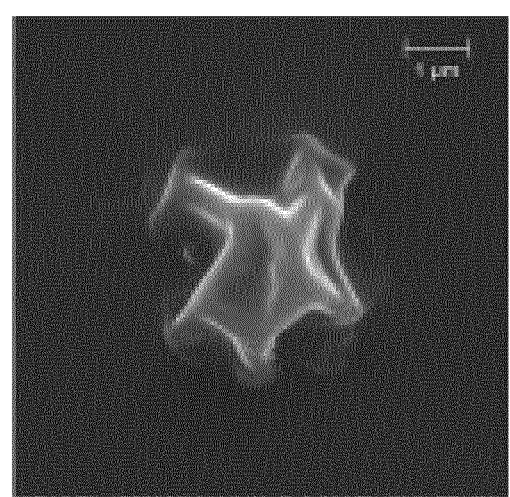
Figure 1A                    Figure 1B
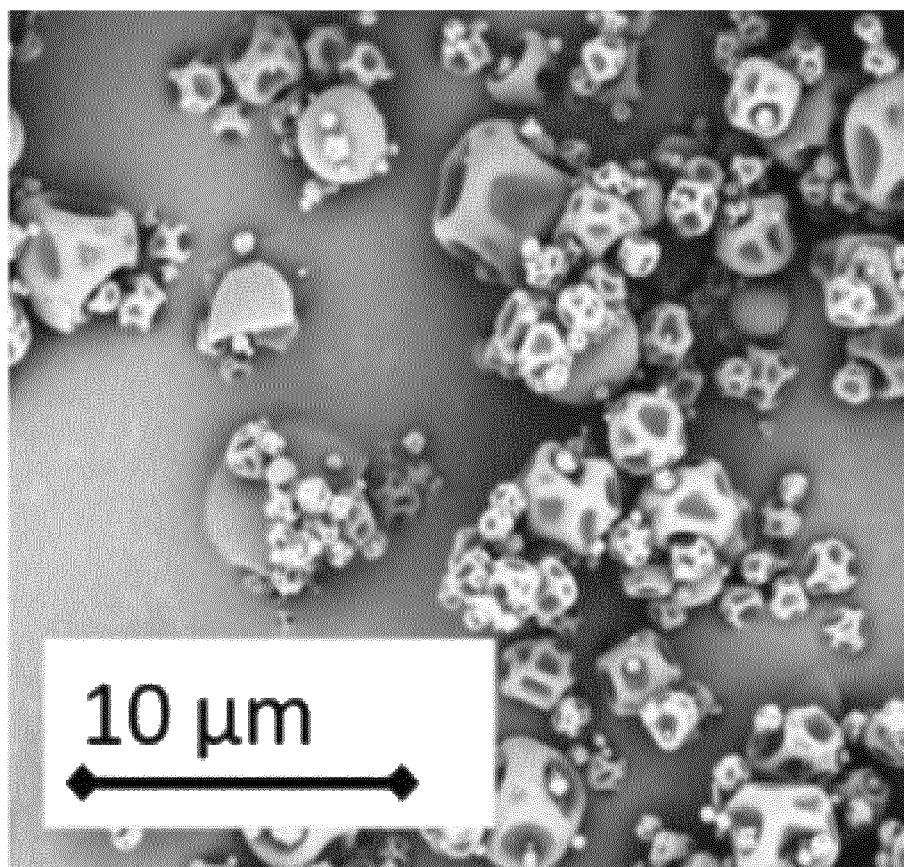
Figure 2

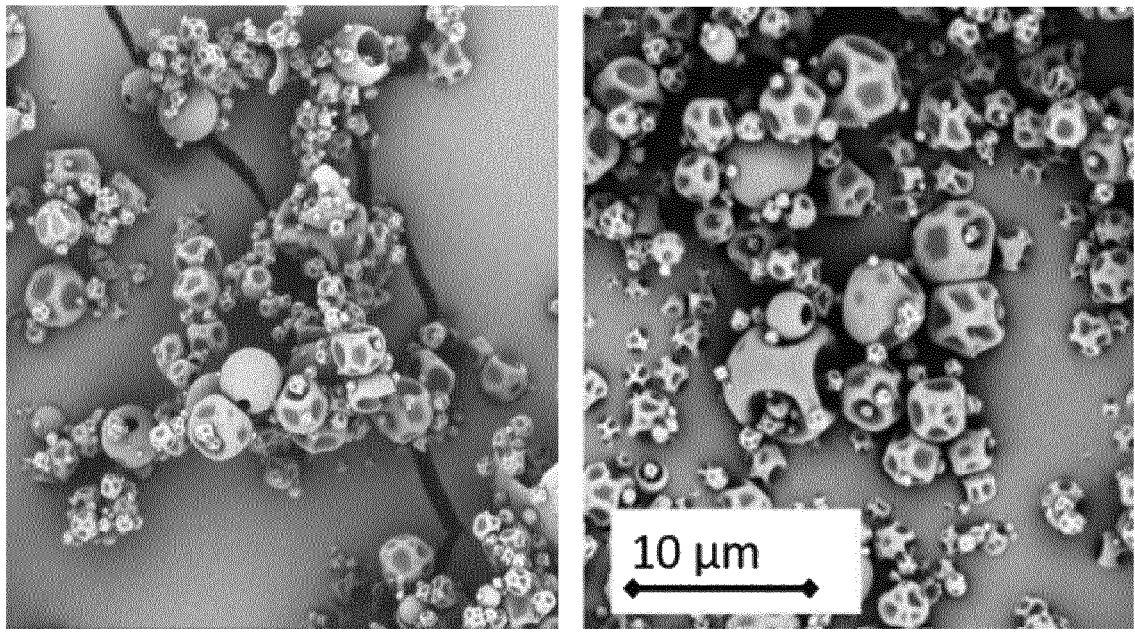
Figure 3                                    Figure 4
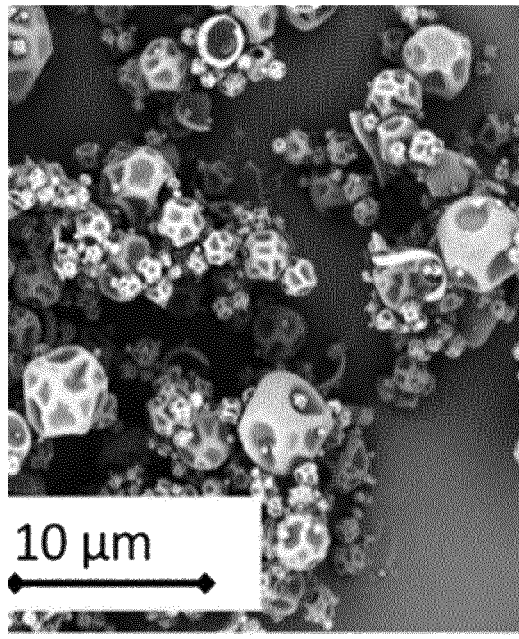
Figure 5

GOLF BALL-LIKE MICROPARTICLES FOR USE IN THE TREATMENT AND PREVENTION OF PULMONARY DISEASES

CROSS REFERENCE TO RELATED APPLICATIONS

This application is a U.S. national phase application claiming priority to International (PCT) Application No. PCT/EP2020/075416 filed Sep. 10, 2020, which claims priority to Belgium patent application no. 2019/5603 filed Sep. 10, 2019. The entire contents of these applications are incorporated herein by reference in their entirety.

TECHNICAL DOMAIN

The present invention relates to a golf ball-like micropar-ticles obtained by atomization of nanosuspensions of nan-oparticles or solutions for dry powder inhalers for use in the treatment and prevention of diseases, in particular pulmo-nary diseases.

PRIOR ART

Inhalation therapy is popular to treat lower respiratory tract infections. In particular, Pulmonary cancer and pulmo-nary inflammations may be treated by inhalation of active pharmaceutical ingredients (API) through dry powder inhal-ers. Many dry powder systems exist: Lactose-carriers with micronized API's on the carrier surface, pellets of micron-ized and agglomerated APIs or porous particles. Existing dry powder formulations may for example only deliver around 30% of the API uniformly throughout the lungs. Whilst lactose is the most widely used carrier, and new carriers are under investigation. For example, raffinose is reported to possess comparable aerosolization performance with tradi-tional lactose carrier.

EP2785326 to the University of North Carolina discloses geometrically engineered molded lactose particles having varied shapes and sizes and surface charge which can incorporate drugs and/or other biomaterials for targeted delivery, such as pulmonary delivery. The particles also may have a range of physical features such as fenestrations, angled arms, asymmetry and surface roughness, charge which alter the interactions with cells and tissues. Engi-neered (mold) shape examples: toroid, helicopter, pollen; dumbbell, boomerang.

CN106924193 to Songwen discloses a high-porosity lac-tose dry powder inhaler carrier and supersaturated synthesis method and applications thereof. The carrier is a flower-shaped porous dry powder particulate with a rough surface. Through a high-porosity nano-pore system.

WO2004052334 to Okpala discloses a method of engi-neering changes in the morphological, chemical or physical features of a particle, to promote, for example, the formation of hairs and pores on the surface of the particle. This document stipulates that contrary to the general trend of the prior art, such rough surfaces in this invention are advanta-geous and promotes roughness of the particle surface by the presence of projections, hairs and/or pores.

Cyclodextrins are mentioned as one of a plurality of suitable excipients.

EP1906919 to Boehringer Ingelheim discloses spray-dried lactase inhalation particles with a formoterol to bude-sonide mass ratio of 1:20. The inhalation particles are described as unagglomerated, discrete, fine, white, easily dispersible powder consisting of mainly toroidal-shaped particles of less than 5 micron in diameter. Cyclodextrins are mentioned as one of a plurality of suitable excipients.

AU2006200277 to Nektar Therapeutics discloses lactose particles with very low bulk density, thus reducing the minimum powder mass that can be filled into a unit dose container of a dry powder inhaler and eliminating the need for carrier particles. The formulations are based on polymer materials and surfactants and may further comprise rigidi-fying excipients, such as dextrose, mannitol, O-mannose, sorbitol, sorbose, lactose, maltose, sucrose, trehalose, raffinose, starches, cyclodextrins and maltodextrins.

Lintingre et al., Control of particle morphology in the spray drying of colloidal suspensions. Soft Matter, Royal Society of Chemistry, 2016, 12 (36), pp. 7435-7444, describes atomized particles in the form of doughnuts or deflated balloons and recommends crumpled paper mor-phologies or hollow spheres for deeper lung deposition.

Cyclodextrins are frequently used as excipients in order to increase the water-solubility of APIs such a budesonide.

For example, EP3151836 to the University of Liege and Paul Maes discloses the use of cyclodextrin in conjunction with the corticosteroid budesonide for the treatment and prevention of bronchial inflammatory diseases.

EP1799231 to the University of Liege proposes the direct administration of cyclodextrins for the treatment of bron-chial inflammatory disease.

Cyclodextrins have been used to compensate for the hygroscopic properties of new carriers such as raffinose which are seen as alternative to the predominantly used lactose carriers.

For example Zhao et al. (2018), Low density, good flowability cyclodextrin-raffinose binary carrier for dry powder inhaler: antihygroscopicity and aerosolization per-formance enhancement, Expert Opinion on Drug Delivery, DOI: 10.1080/17425247.2018.1450865, discloses Cyclo-dextrin-raffinose binary carriers produced by spray-drying for reducing the hygroscopicity-induced agglomeration of raffinose carriers. Cyclodextrin is used as antihygroscopic excipient. It teaches that the addition of HP-beta-CD in dry powder inhaler formulations can inhibit the access of mois-ture to raffinose, surmounting the hygroscopicity and the associated agglomeration. The spray-dried particles of Zhao are described as a core-shell structure formed of a core of raffinose and a shell of cyclodextrin and to appear as jujube-like microstructure with a rough surface in scanning electron microscopy.

However, this disclosure only teaches a binary cyclodex-trin-raffinose carrier system.

Dufour, et al. Int J Pharm. 2015 November 30; 495(2): 869-78, hereinafter referred to as Dufour 2015, assesses the aerodynamic behavior of budesonide/HPBCD spray-dried powder compared to a formulation comprising budesonide and lactose as a carrier and the impact of a "deflated-ball like" shape as shown in FIG. 1B on aerodynamic properties of the spray-dried powder. It claims that higher budesonide respirable fraction and lower permeability through lung epithelium are of interest in the management of inflamma-tion associated with asthma. The surface depressions of the microparticles shown in Dufour 2015 are shown in com-parative FIG. 1A and are characterized by an increased deflation. Average depth of the surface depressions (1) is 40% or even 45% or more as compared to the average maximum diameter of the microparticles of Dufour 2015 shown in FIG. 1A. The fine particle fraction (FPF) is 44,05%. The increased deflation of the microparticles of Dufour 2015 adversely impacts the flight stability and flight trajectory of such microparticles in the respiratory system.

Moreover, the increased deflation of Dufour increases stickiness of the microparticles and reduces flowability.

There is therefore a need fora simple and yet more effective carrier system in view of enabling a uniform and homogenous deposition of an API in and throughout the lungs of mammals. In particular, there is need for carrier systems that haven improved flight stability, Fine Particle Fraction and a reduced stickiness as compared to Dufour 2015.

SHORT SUMMARY OF THE INVENTION

The present inventors now have surprisingly found, that spray-drying of improved cyclodextrin formulations directly lead to golf-ball like microparticles that might enable an improved and uniform deposition of one or more API's throughout the lungs for the treatment and prevention of any disease, in particular of lung cancer, pulmonary inflammations or other pulmonary diseases. In particular, the present inventors have found that both the fine particle fraction and the aerodynamic stability of spray-dried cyclodextrin formulations may be further improved through the golf-ball like shape. Also, the Fine Particle Fraction of the plurality of microparticles according to the present invention is increased over Dufour 2015 with 50% or more against the 44,05% of Dufour. Moreover, the microparticles of the present inventions are less sticky than the particles of Dufour 2015.

Accordingly, the present invention relates to a plurality of microparticles, in particular spherical microparticles, for use in the treatment and prevention of respiratory diseases comprising one or more carriers and one or more active pharmaceutical ingredients, wherein a. the microparticles have a median mass aerodynamic diameter of 0.1 microns or more and 5 microns or less or a diameter of 0.1 microns or more and 10 microns or less;

b. the microparticles have a core-shell structure, with the carrier forming the shell and the active pharmaceutical ingredient forming the core;

c. the microparticles have a substantially spherical shape with a plurality of golf ball-like surface depressions identifiable by scanning electron microscopy;

d. the average depth of the surface depressions (1) is 5% or more and 30% or less as compared to the average maximum diameter of the microparticles;

e. 50 surface area % or more as compared to the total surface of the microparticles are depressed; optionally f. a Fine Particle Fraction of 50% or more.

In another embodiment, the surface depressions are arranged in a substantially symmetrical way.

In another embodiment, the carrier is selected from one or more carriers chosen from the group consisting of alpha-cyclodextrin, beta-cyclodextrin and γ-cyclodextrin, 2-hydroxypropyl-beta-cyclodextrin (HPBCD), 2-hydroxypropyl-γ-cyclodextrin (HPGCD), sulfobutylether-beta-cyclodextrin (SBEBCD), and methyl-beta-cyclodextrin (MBCD).

In another embodiment, the carrier is hydroxypropyl-beta-cyclodextrin.

In another embodiment, the carrier is present in an amount of 90 w. % or more as compared to the total weight of the microparticle.

In another embodiment, the carrier is present in an amount of 95 w. % or more as compared to the total weight of the microparticle.

In another embodiment, the one or more active pharmaceutical ingredients are selected from the group consisting of corticosteroids, bronchodilators, antibacterial or anti-inflammatory compounds or combinations thereof.

In another embodiment, the one or more active pharmaceutical ingredient is budesonide or formoterol or a combination thereof.

In another embodiment, the molar ratio of the active pharmaceutical ingredient and the carrier is 1:1.

In another embodiment, the microparticles further comprise amino acids. In another embodiment, the microparticles further comprise leucine.

In another embodiment, the microparticles are obtained by spray-drying.

A further object of the present invention is the use of microparticles of the invention for delivering an active pharmaceutical ingredient through the respiratory system or the pulmonary system.

A further object of the present invention is the use of microparticles for delivering an active pharmaceutical ingredient through the respiratory system or the pulmonary system comprising one or more carriers and one or more active pharmaceutical ingredients, wherein a. the microparticles have a median mass aerodynamic diameter of 0.1 microns or more and 5 microns or less;

b. the microparticles have a core-shell structure, with the carrier forming the shell and the active pharmaceutical ingredient forming the core;

c. the microparticles have a plurality of golf ball-like surface depressions identifiable by scanning electron microscopy;

d. the average maximum depth d of the surface depressions (1) is 5% or more and 30% or less as compared to the average maximum diameter D of the microparticles; and e. 50 surface area % or more as compared to the total surface of the microparticles are depressed; and optionally f. the Fine Particle Fraction of the plurality of microparticles is 50% or more.

A further object of the present invention is the use of the microparticles of the invention for delivering an active pharmaceutical ingredient through the respiratory system or the pulmonary system, wherein the active pharmaceutical ingredient is an active pharmaceutical ingredient for the treatment or prevention of asthma, chronic obstructive pulmonary disease (COPD), pulmonary fibrosis, pneumonia, and lung cancer.

A further object of the present invention is the use of microparticles for the treatment or prevention of asthma, chronic obstructive pulmonary disease (COPD), pulmonary fibrosis, pneumonia, and lung cancer.

Another aspect of the invention is a method of treatment of a disease, in particular a respiratory disease, comprising one or more carriers and one or more active pharmaceutical ingredients, wherein a. the microparticles have a median mass aerodynamic diameter of 0.1 microns or more and 5 microns or less;

b. the microparticles have a core-shell structure, with the carrier forming the shell and the active pharmaceutical ingredient forming the core;

c. the microparticles have a plurality of golf ball-like surface depressions identifiable by scanning electron microscopy;

d. the average maximum depth d of the surface depressions (1) is 5% or more and 30% or less as compared to the average maximum diameter D of the microparticles; and e. 50 surface area % or more as compared to the total surface of the microparticles are depressed;

wherein the microparticles are administered per inhalation in an amount effective to reduce, stabilize or positively impact the symptoms of the disease, in particular the respiratory disease, preferably without causing treatment limiting side effects, such as those selected from the group consisting of renal clearance, hepatic impairment as expressed by elevated levels of transaminase, and wheezing after administration, as compared to subjects untreated with the microparticles of the invention. In another embodiment of the method of the present invention, the disease is a respiratory disease selected from the group consisting of asthma, chronic obstructive pulmonary disease (COPD), pulmonary fibrosis, pneumonia, and lung cancer.

A further object of the present invention is a process for the manufacturing of microparticles of the invention, comprising the steps of:

a. mixing of one or more carriers and one or more active pharmaceutical ingredients to obtain a nanosuspension or a solution.

b. spray-drying of the nanosuspension or solution of step a.

DETAILED DESCRIPTION OF THE INVENTION

Other characteristics and advantages of the present invention will be derived from the non-limitative following description, and by referring to the drawings and the examples.

Particles of the present invention may be obtained by atomization or spray drying of a liquid formulation.

Accordingly, the present invention relates to a plurality of microparticles, in particular spherical microparticles, for use in the treatment and prevention of respiratory diseases comprising one or more carriers and one or more active pharmaceutical ingredients, wherein a. the microparticles have a median mass aerodynamic diameter of 0.1 microns or more, preferably 0.5 microns or more; in another embodiment, the microparticles have a median mass aerodynamic diameter of 10 microns or less, preferably 5 microns or less, even more preferably 3 microns or less or a diameter of 0.1 microns or more, preferably, 1 microns or more and even more preferably 3 microns or more and 10 microns or less, preferably 7 microns or less, even more preferably 5 microns or less.

b. the microparticles have a core-shell structure, with the carrier forming the shell and the active pharmaceutical ingredient forming the core; and c. the microparticles have a substantially spherical shape with a plurality of golf ball-like surface depressions identifiable by scanning electron microscopy d. the average depth of the surface depressions (1) is 5% or more and 30% or less as compared to the average maximum diameter of the microparticles; and e. the depressed surface (1) is 50% or more as compared to the total surface of the microparticles; optionally f. the surface depressions are arranged in a substantially symmetrical way; optionally g. the Fine Particle Fraction is 50% or more.

Golf-ball like surface depressions are areas on the surface of the spherical microparticles that are deflated, as for example the surface area (1) shown in FIG. 2A and FIG. 2B. The golf-ball like surface depressions have the advantage of increased and uniform deposition when inhaled for example with a dry powder inhaler. Consequently, the microparticles of the present invention appear like golf balls under a scanning electron microscope.

Substantially spherical in the sense of the present inventions means is a an essentially round geometrical shape, in particular an essentially round ball, like for example shown in FIGS. 2A and 2B. Some variations may be acceptable since the spherical microparticles of the present inventions are obtainable by spray drying. In particular, the spherical microparticles of the invention resemble a golf ball. Whilst a golf ball may be precisely molded, the microparticles of the present invention are obtainable by spray-drying. Consequently, variations in the spherical shape and the surface depression as well as the symmetry associated with micronization of nanosuspensions through atomization or spray-draying are inevitable. This is why average dimensions are used to describe the dimensional choices that give the golf-ball like microparticles their flight or trajectory stability.

The average maximum depth d is measured using scanning electron microscopy (SEM) images. An average may for example be assessed by measuring 5, 10, 15, 20, 25, 50 or even 100 microparticles and calculating the arithmetic means. FIG. 7 illustrates in an exemplary and simplified way, how the maximum depth of a surface depression (1) may be measured.

A first line (2) is drawn between two opposing border points of the surface depression. A second line (3) is drawn parallel to the first line (2) and going through the deepest point of the surface depression (1). In a third step the maximum depth d is evaluated. Some variations may be acceptable since the microparticles of the present inventions are obtainable by spray drying.

The average maximum diameter D is measured using scanning electron microscopy images, preferably by either a Philips XL30 ESEM, or a FEI Quanta 600 after metallization with Au (~50 nm). An average may for example be assessed by measuring 5, 10, 15, 20, 25, 10 or even 100 microparticles and calculating the arithmetic means. FIG. 9 illustrates in an exemplary and simplified way, how the maximum depth of a surface depression (1) may be measured. Two lines (4) and (5) are drawn between two opposing points of the microparticle with the provision that the surface depressions are ignored and a hypothetical surface without depressions is taken. In a second step the maximum distance D is evaluated. Some variations may be acceptable since the microparticles of the present inventions are obtainable by spray drying.

In another embodiment, the average maximal depth d of the surface depressions (1) is 30% or less, preferably, 25% or less, even more preferably 20% or less, even more preferably 15% or less as compared to the maximum diameter D of the microparticle as measurable with a scanning electron microscope. Some variations may be acceptable since the microparticles of the present inventions are obtainable by spray drying.

In another embodiment, the average maximal depth d of the surface depressions (1) is 5% or more, preferably, 7,5% or more, even more preferably 10% or less, even more preferably 12,5% or more as compared to the maximum diameter D of the microparticle as measurable with a scanning electron microscope. Some variations may be acceptable since the spherical microparticles of the present inventions are obtainable by spray drying.

In another embodiment, the average depressed surface (1) is 50% or more, preferably 60% or more, even more preferably 70% or more as compared to the total surface of the microparticle as measurable with a scanning electron microscope. Some variations may be acceptable since the spherical microparticles of the present inventions are obtainable by spray drying.

The average depressed surface is measured using scanning electron microscopy images. An average may for example be assessed by measuring 5, 10, 15, 20, 25, 10 or even 100 microparticles and calculating the arithmetic means. FIG. 9 illustrates in an exemplary and simplified way an exemplary surface depression (1) at the example of the black surface 6.

In another embodiment, the depressed surface (1) is 95% or less, preferably 90% or less, even more preferably 80% or less as compared to the total surface of the microparticle as measurable with a scanning electron microscope. Some variations may be acceptable since the microparticles of the present inventions are obtainable by spray drying.

In another embodiment, the Fine Particle Fraction as compared to the residual dose described below is 50% or more, preferably, 55% or more, even more preferably 60% or more, even more preferably 65% or more, even more preferably 70% or more, even more preferably 75% or more and even more preferably 80% or more. In particularly preferred embodiment the Fine Particle Fraction is 85% or more and even more preferably 90% or even 95% or more. Some variations may be acceptable since the microparticles of the present inventions are obtainable by spray drying.

In another embodiment, the Fine Particle Fraction (FPF) of the plurality of microparticles of the present invention is measured using Next Generation Impacter with three repetitions. Preferably the pulmonary deposition profile of the powder produced during spray drying is determined in vitro by a New Generation Impactor (NGI). The device, a dry powder inhaler, is connected to the induction port by a mouthpiece mimicking the mouth. The NGI is divided into 8 stages characterized by a pore diameter covering a particle size range between 0.206 μm and 12.8 μm. A pump, connected to the NGI, allows the pressure and flow to be adjusted. Twelve capsules, containing a known mass of powder, are perforated by the device, of the Aerolizer® type, and emptied of their contents. This passes through the NGI at a flow rate of 100 mL/min for a period of 2.4 seconds. Once these twelve capsules have been introduced, the powder deposited at each level is recovered using a methanol/water solvent (65/35 V/V) and analyzed by HPLC. The total mass measured after each test in the throat and in stages 1 to 8 is defined as the recovered dose (RD). The fine particle dose (FPD) is defined as the total mass ranging from 0 μm to 5 μm. The fine particle fraction is calculated by dividing the FPD by the RD expressed as a percentage.

In another embodiment, the carrier is selected from one or more carriers chosen from the group consisting of alpha-cyclodextrin, beta-cyclodextrin and γ-cyclodextrin, or pharmaceutically acceptable derivatives thereof, for example 2-hydroxypropyl-beta-cyclodextrin (HPBCD), 2-hydroxypropyl-γ-cyclodextrin (HPGCD), sulfobutylether-beta-cyclodextrin (SBEBCD), and methyl-beta-cyclodextrin (MBCD).

In another embodiment, the carrier is hydroxypropyl-beta-cyclodextrin.

In another embodiment, the carrier does not contain any cyclodextrin-raffinose.

In another embodiment, the carrier is present in an amount of 80 w % or more, preferably, 85 w % or more, even more preferably 90 w % or more and even more preferably 95 w % and even more preferably 97,5 w % or more as compared to the total dry weight of the microparticle.

In another embodiment, the carrier is present in an amount of 99 w. % or more as compared to the total weight of the microparticle.

In another embodiment, the one or more active pharmaceutical ingredients are selected from the group consisting of corticosteroids, anti-inflammatory compounds and combinations thereof. In another embodiment, the one or more active pharmaceutical ingredients are budesonide or formoterol or a combination thereof.

In another embodiment, the active pharmaceutical ingredient is present in an amount of 0,01 w % or more, preferably, 0,1 w % or more, even more preferably 0,5 w % or more and even more preferably 0,75 w % and even more preferably 0,90 w % or more as compared to the total dry weight of the microparticle.

In another embodiment, the active pharmaceutical ingredient is present in an amount of 5 w % or less, preferably 2,5 w % or less, even more preferably 1 w % or less as compared to the total dry weight of the microparticle.

In another embodiment, no active pharmaceutical ingredient is present. In this embodiment, the microparticles are formed of the carrier, in particular of a cyclodextrin carrier, and in particular of a cyclodextrin carrier not containing raffinose.

In another embodiment, the molar ratio of the active pharmaceutical ingredient and the carrier is 1:1.

In another embodiment, the microparticles further comprise amino acids. In another embodiment, the microparticles further comprise leucine.

In another embodiment, the microparticles are obtained by spray-drying.

A further object of the present invention is the use of microparticles of the invention for delivering an active pharmaceutical ingredient through the respiratory system or the pulmonary system. It has been surprisingly found that the morphology of the particles primarily is responsible for an effective delivery of any active pharmaceutical ingredient through the respiratory system, in particular the pulmonary system. Consequently, the active pharmaceutical composition may also be for the treatment of other diseases than respiratory diseases.

A further object of the present invention is the use of the microparticles of the invention for delivering an active pharmaceutical ingredient through the respiratory system or the pulmonary system, wherein the active pharmaceutical ingredient is an active pharmaceutical ingredient for the treatment or prevention of asthma, chronic obstructive pulmonary disease (COPD), pulmonary fibrosis, pneumonia, and lung cancer.

A further object of the present invention is the use of microparticles for the treatment or prevention of asthma, chronic obstructive pulmonary disease (COPD), pulmonary fibrosis, pneumonia, and lung cancer.

A further object of the present invention is a process for the manufacturing of microparticles of any of the preceding claims, comprising the steps of:

a. mixing of one or more carriers and one or more active pharmaceutical ingredients with water or other suitable polar solvents and optionally other ingredients to obtain a nanosuspension or a solution.

b. spray-drying of the nanosuspension or solution of step

The solution or nanosuspension of the invention is obtained by mixing with a polar solvent, preferably water.

The liquid formulation for atomization or spray-drying may comprise one or more excipients. In a preferred embodiment, the excipient selected from the group consisting of lactose, mannitol, raffinose, maltodextrin and cyclodextrins, in particular HP-beta-CD and combinations thereof.

In another embodiment of the spray drying process of the current invention, the API, in particular budesonide and formoterol and the one or more excipients are dissolved or suspended.

The process parameters of the atomization of the present invention may vary widely. Any parameters may be chosen that deliver the golf ball-like structure of the present invention.

The gas temperature typically is from 100° C. to 200° C., preferably from 110° C. to 150° C., and more preferably from 115° C. to 145° C.

Liquid feed rate may vary widely and typically is from 200 to 500 ml/h, preferably from 350 and 450 ml/h, even more preferably from 375 and 450 25 ml/h.

In another embodiment, the nozzle of the atomization unit is chosen to allow for micronization through the formation of microparticles of the size of 0.1 to 5 microns.

The obtained particles have physico-chemical properties that allow of uniform and homogenous deposition of one or more APIS throughout the lung with increased delivery rates.

The golf-ball like shape may be determined using standard two- and three-dimensional technologies, for example microtomography RX. Suitable devices are commercially available under the commercial brand Skyscan 1172.

Another suitable technology is Environmental Scanning Electron Microscope (ESEM) XL30 FEI, with variable pressure control and X-ray microanalysis.

2D morphology of the particles of the present invention may also be measured by Transmission electron microscopy.

The uniform deposition of the particles of the present invention may be further measured for example by Functional Respiratory Imaging (FRI) technology, available for example from Fluidda using for example Computer Tomography (CT) scans.

DRAWINGS

FIG. 1A is a comparative SEM image of a "deflated-ball like" shape of the prior art (Dufour 2015).

FIG. 1B is a comparative SEM image of the jujube-like cyclodextrin-raffinose binary carriers of the prior art (Zhao 2018).

FIG. 2A is an SEM image of an embodiment of a golf-ball like microparticle of the present invention comprising budesonide and a hydroxypropyl-beta-cyclodextrin carrier.

FIG. 2B is an SEM image of an embodiment of a plurality of golf-ball like microparticles of the present invention comprising budesonide and a hydroxypropyl-beta-cyclodextrin carrier.

FIG. 3 is an SEM image of an embodiment of a plurality of golf-ball like microparticles of the present invention comprising budesonide, a hydroxypropyl-beta-cyclodextrin carrier and 1 w % leucine.

FIG. 4 is an SEM image of an embodiment of a plurality of the golf ball-like microparticles of the present invention comprising budesonide, a hydroxypropyl-beta-cyclodextrin carrier and 2 w % leucine.

FIG. 5 is an SEM image of an embodiment of a plurality of the golf ball-like the microparticles of the present invention comprising budesonide, a hydroxypropyl-beta-cyclodextrin carrier and 5 w % leucine.

FIG. 100 is an SEM image of an embodiment of a plurality of the golf ball-like microparticles of the present invention according to example 22.

Figure 15:
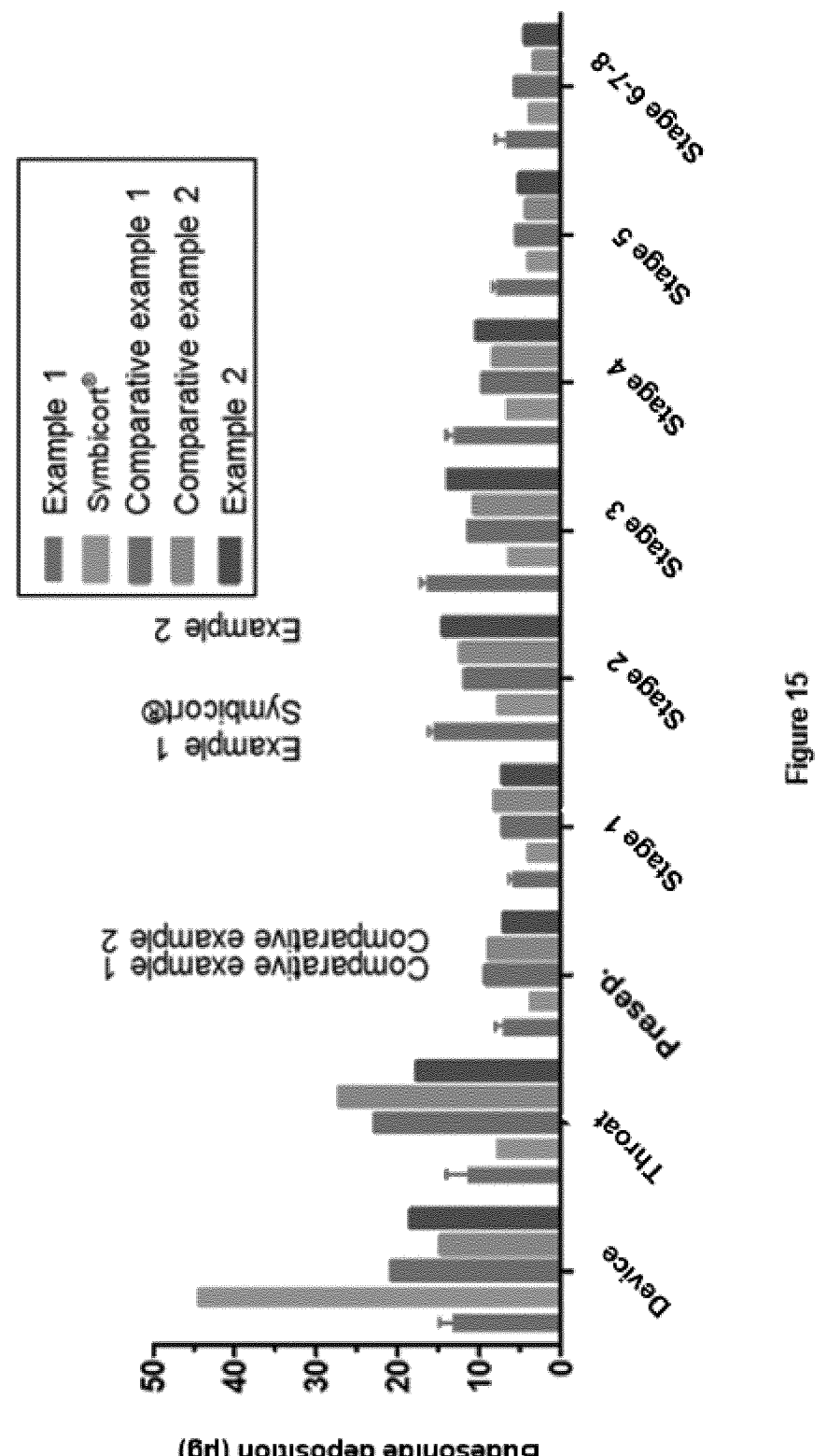

FIG. 15 shows the NGI deposition of budesonide of examples 1 and 2, comparative examples 1 and 2 and Symbicort.

Figure 16:
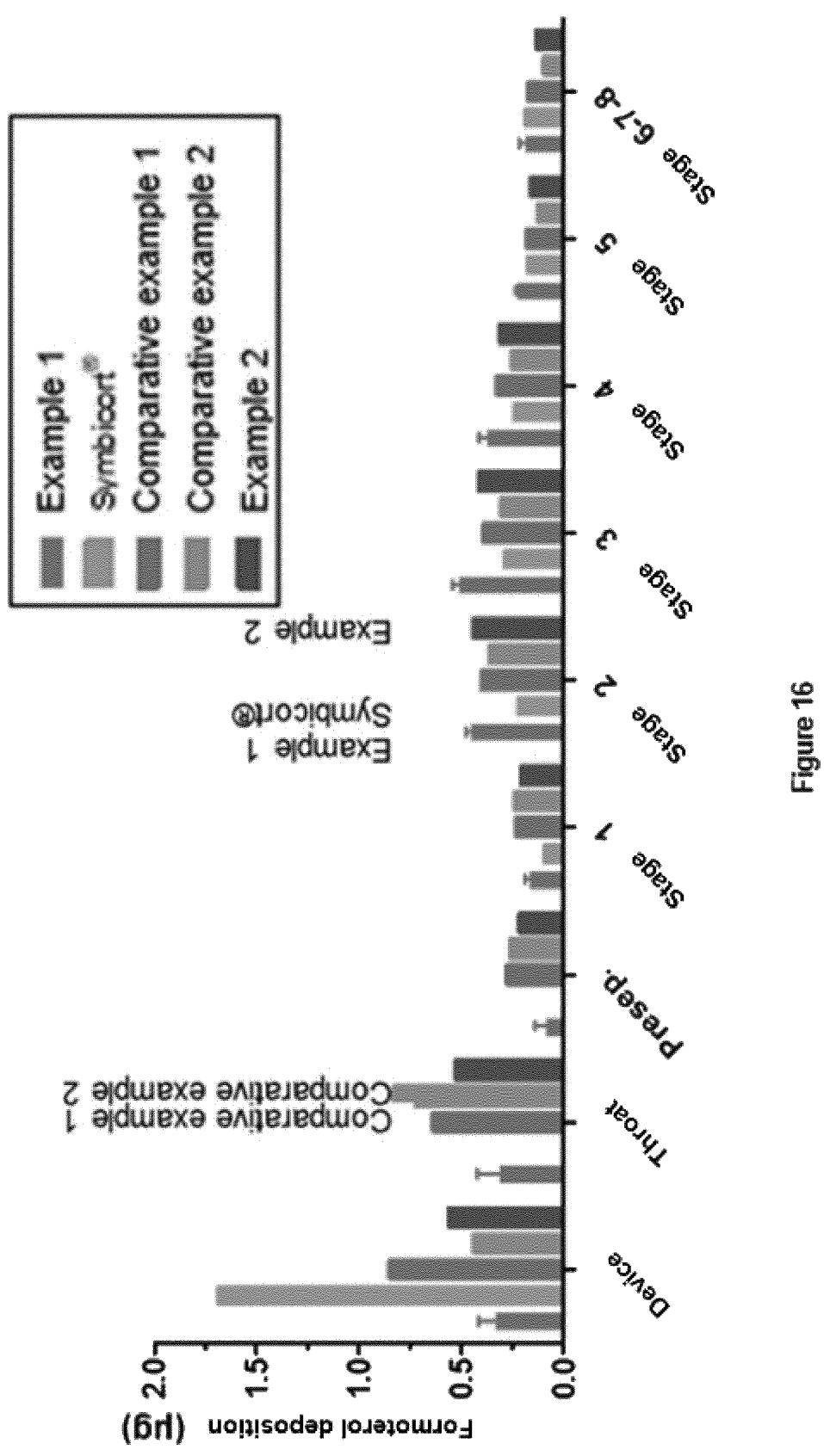

FIG. 16 shows the NGI deposition of formoterol of examples 1 and 2, comparative examples 1 and 2 and Symbicort.

Figure 17:
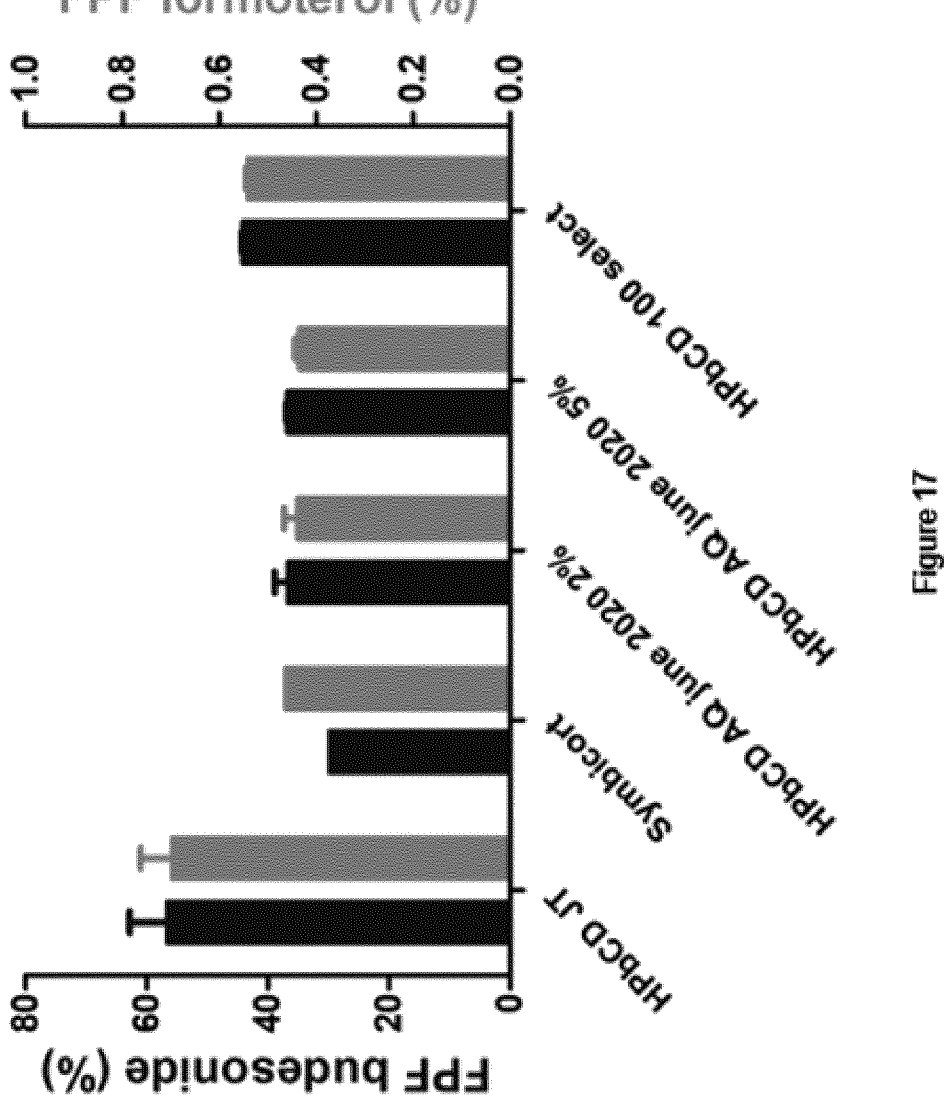

FIG. 17 shows the Fine Particle Fraction of examples 1 and 2, comparative examples 1 and 2 and Symbicort.

Figure 18:
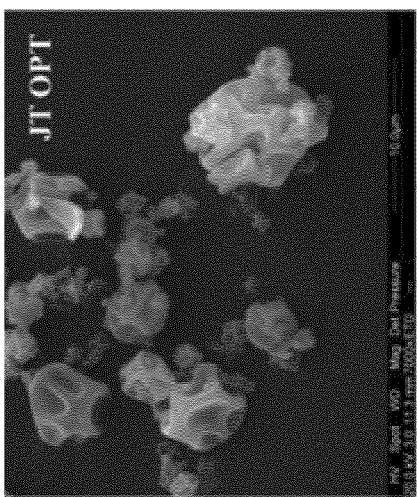

FIG. 18 is an SEM picture of the golf-ball like microparticles according to example 3 also referred to as JT OPT.

Figure 19:
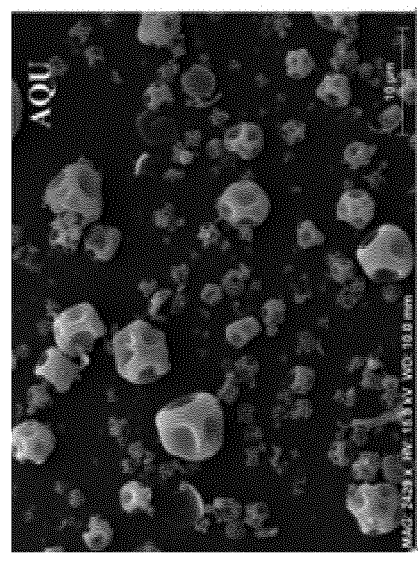

FIG. 19 is an SEM picture of the golf-ball like microparticles according to example 4 also referred to as AQU.

Figure 20:
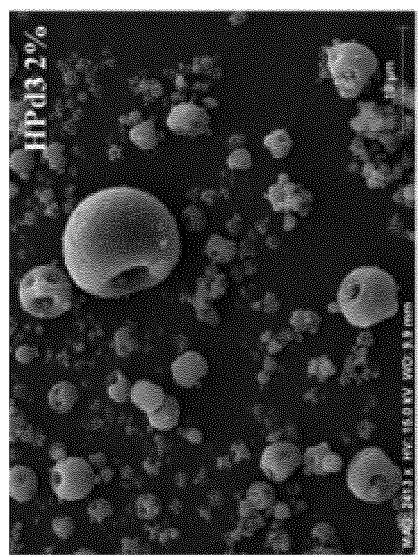

FIG. 20 is an SEM picture of less deflated balls according to comparative example 3 also referred to as HPd3 2%.

Figure 21:
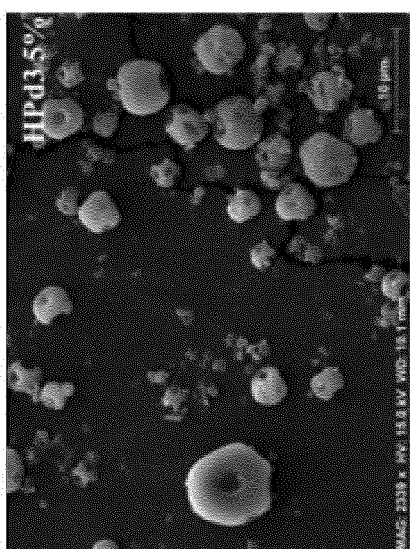

FIG. 21 is an SEM picture of less deflated balls according to comparative example 4 also referred to as HPd3 5%.

Figure 22:
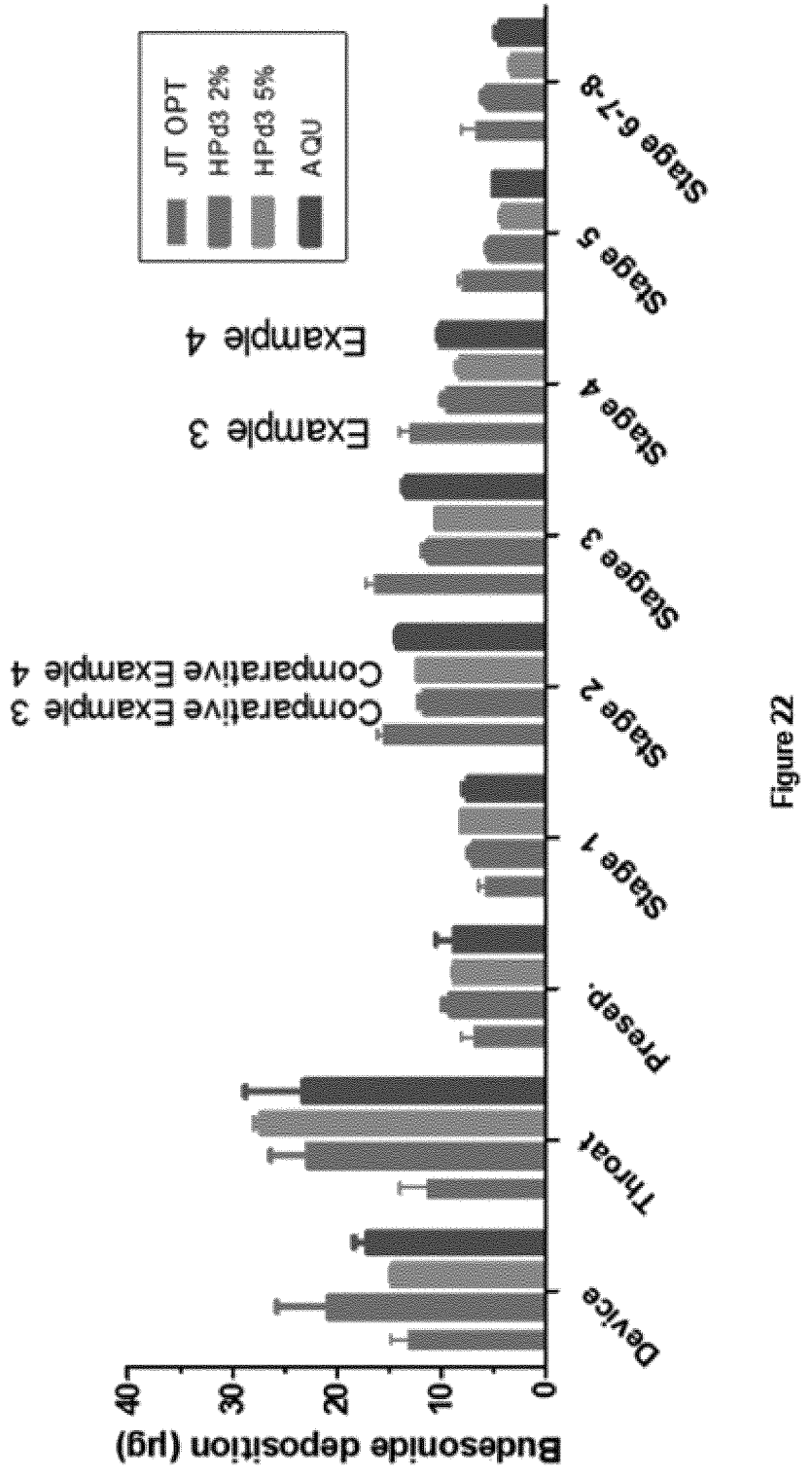

FIG. 22 is an evaluation of budesonide lung deposition evaluated in vitro with NGI apparatus of examples 3 and 4 and comparative examples 3 and 4 with three repetitions.

Figure 23:
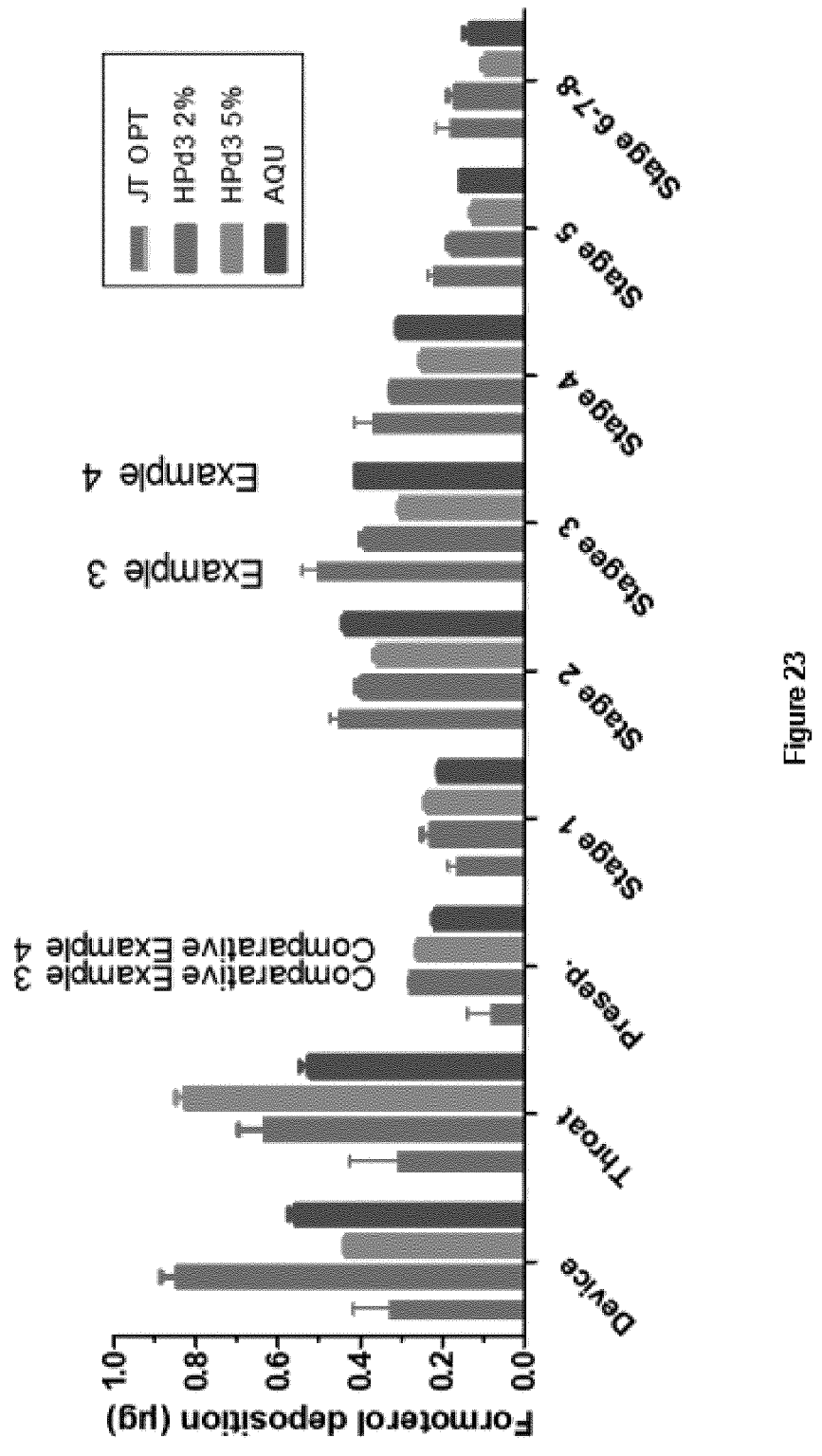

FIG. 23 is an evaluation of formoterol lung deposition evaluated in vitro with NGI apparatus of examples 3 and 4 and comparative examples 3 and 4 with three repetitions.

Figure 25:
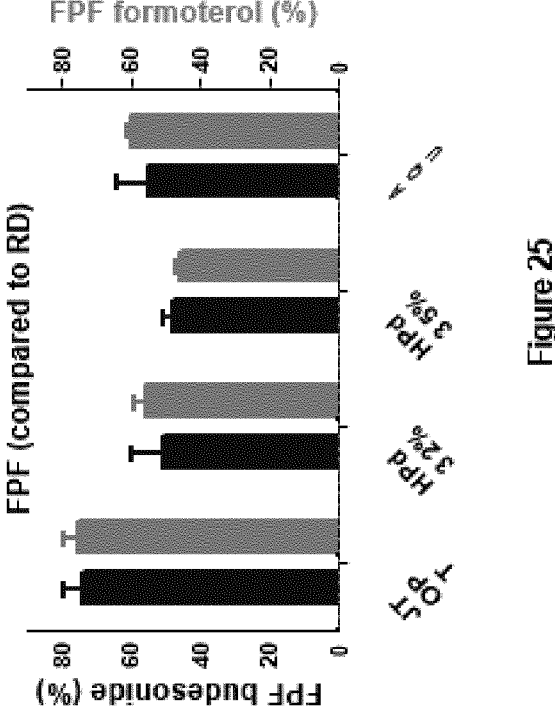
Figure 24:
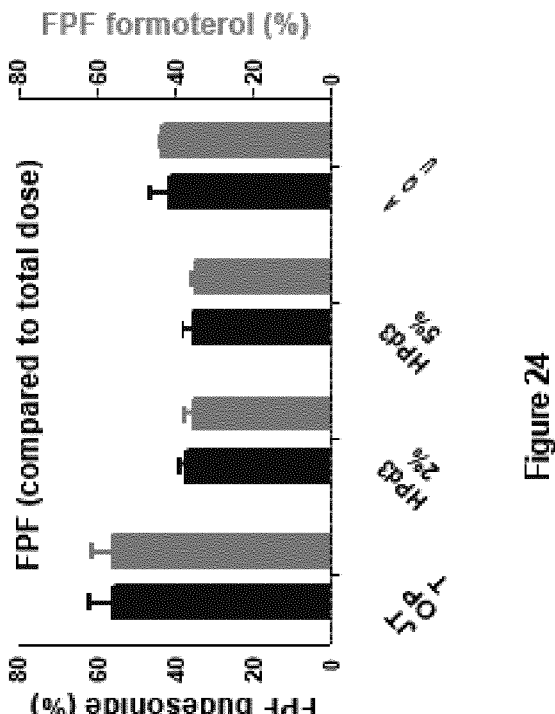

FIGS. 24 and 25 show of the Fine Particles Fraction (FPF) obtained for the four powders using NGI apparatus. FPF was calculated compared to the total dose powder or compared to the Recovery Dose (RD=powder in throat, pre-separator and all stages) n=3.

Figure 26:
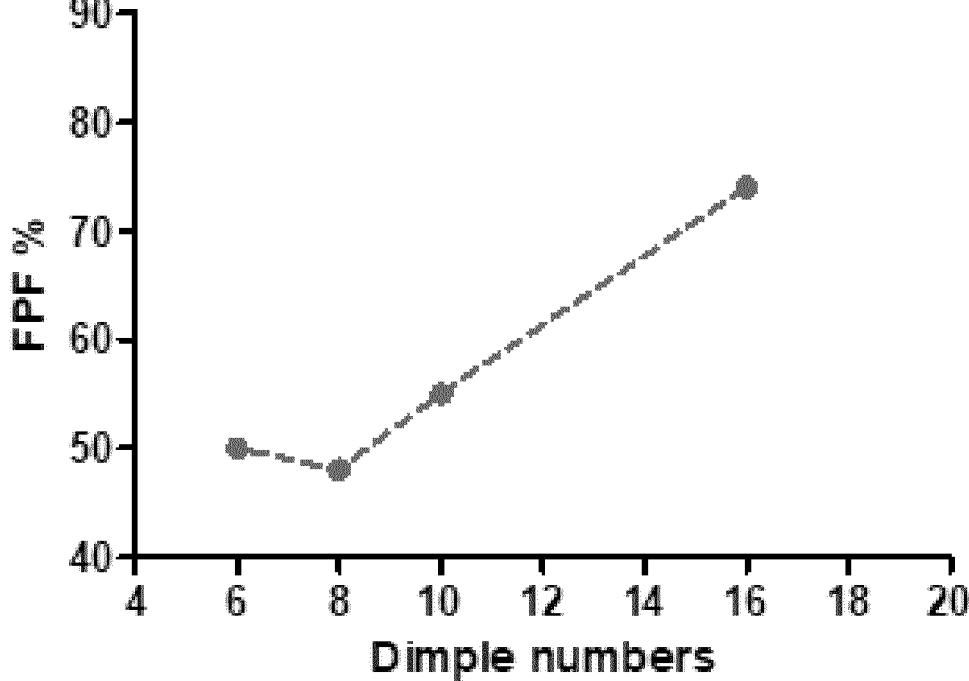

FIG. 26 shows the correlation between Fine Particles Fraction (FPF—compared to RD) and the number of surface depressions—also referred to as dimple numbers—observed on SEM pictures of examples 3 and 4 and comparative examples 3 and 4.

In the drawings, the same reference numbers have been allocated to the same or analog element.

EXAMPLES

Examples 1 and 2

Example 1 also referred to as HPbCD JT shows microparticles according to the invention comprising hydroxypropyl-beta-cyclodextrin (HPBCD) as carrier and budesonide and formoterol as active pharmaceutical ingredients. 99; 29 w % of the dry weight are HPBCD and 0,0.71 of the dry weight of the solution are active pharmaceutical ingredient. 97 w % of the active pharmaceutical ingredient are budesonide and 3 w % of the active pharmaceutical ingredient are formoterol.

Figure 6:
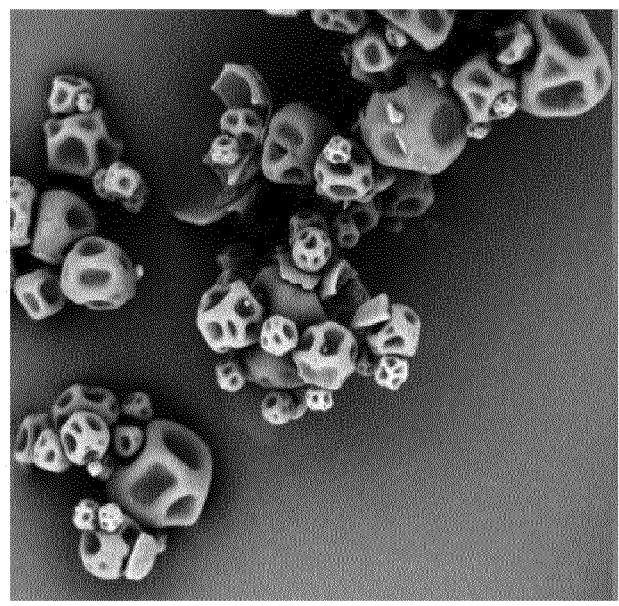
FIG. 6 is an SEM image of an embodiment of a plurality of the golf ball-like microparticles of the present invention comprising budesonide, a hydroxypropyl-beta-cyclodextrin carrier and formoterol.
Figure 7:
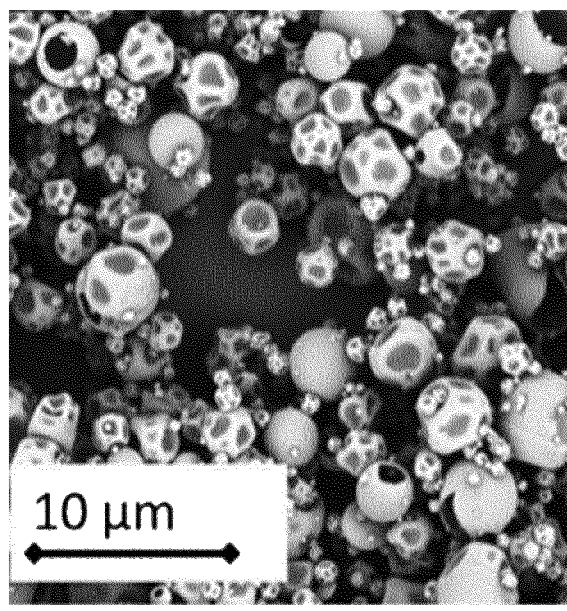
FIG. 7 is an SEM image of an embodiment of a plurality of the golf ball-like microparticles of the present invention comprising budesonide, a hydroxypropyl-beta-cyclodextrin carrier, formoterol and 2 w % leucine.
Figure 8:
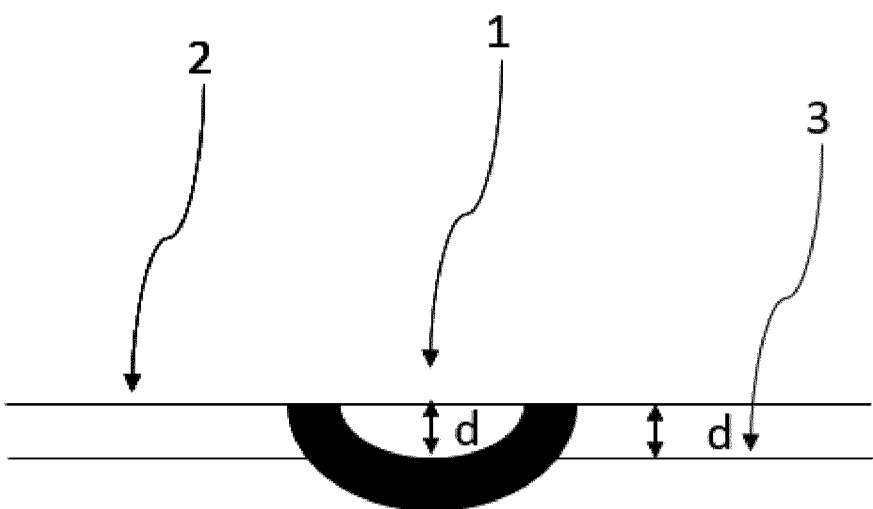
FIG. 8 is a simplified schematic drawing of the measurement of the maximal depth of a surface depression of a golf-ball like microparticle of the present invention.
Figure 9:
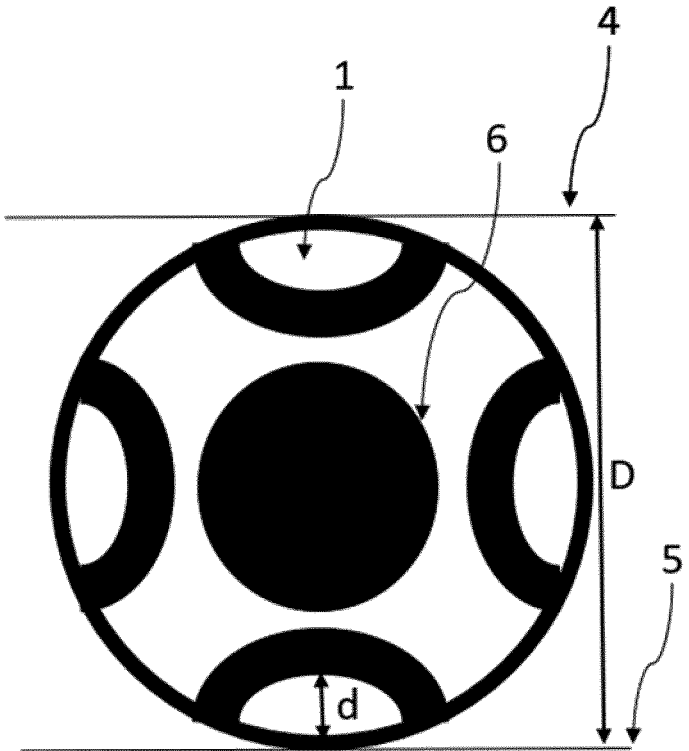
FIG. 9 is a simplified schematic drawing of the measurement of the maximal diameter of a golf-ball like microparticle of the present invention.
Figure 10A:
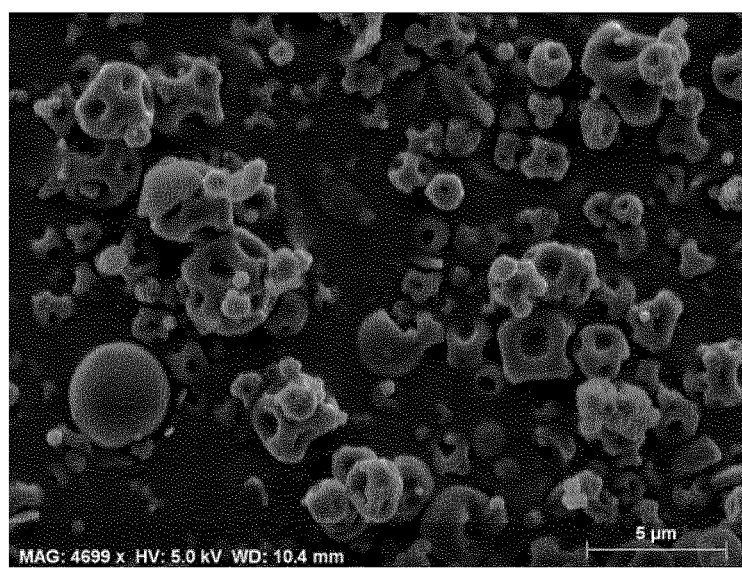
FIG. 10A is an SEM image of an embodiment of a plurality of the golf ball-like microparticles of the present invention according to example 20.
Figure 10B:
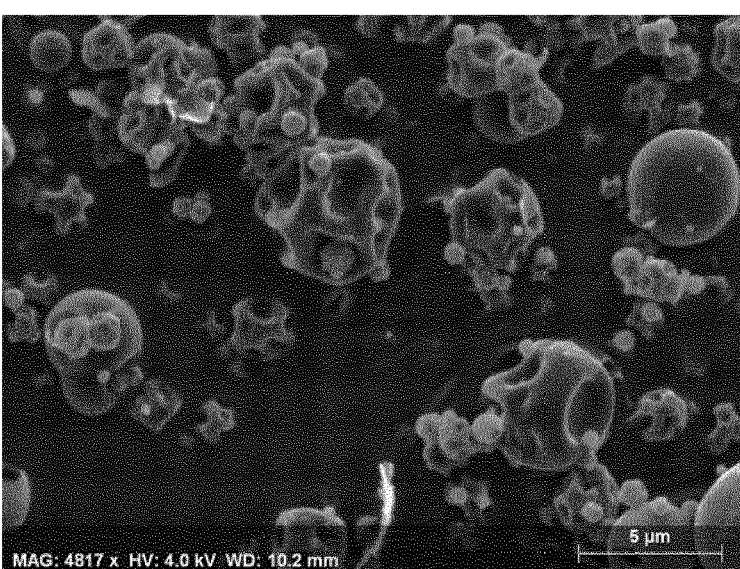
FIG. 10B is an SEM image of an embodiment of a plurality of the golf ball-like microparticles of the present invention according to example 21.
Figure 10C:
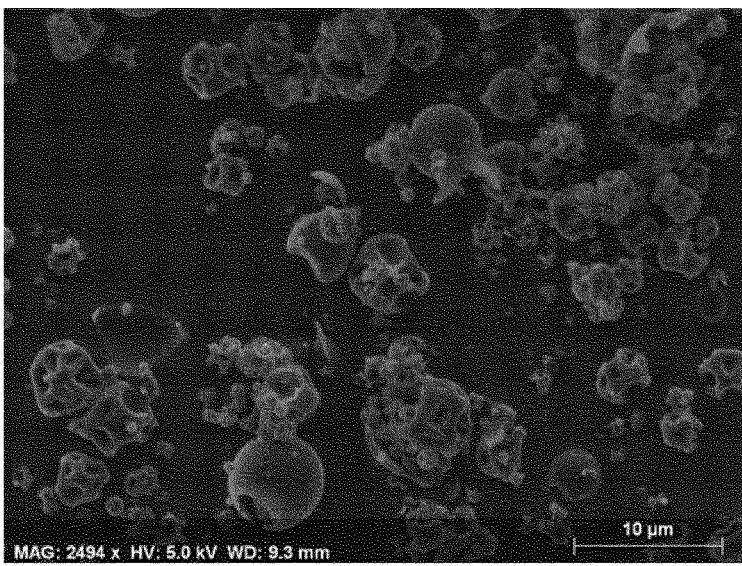
Figure 11:
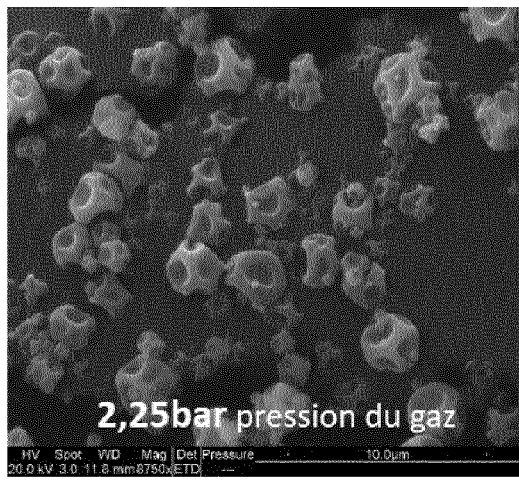
FIG. 11 is an SEM image of an embodiment of a plurality of the golf ball microparticles of the present invention according to example 1.

The microparticles of example 1 are obtained by spray-drying with 10 w % HPBCD of the dry weight, a nozzle diameter of 0.5 mm, an inlet temperature of 160° C., a pump speed of 50 RPM and a nozzle gas pressure 2.25 bar. The SEM is shown in FIG. 11.

Figure 12:
FIG. 12 is an SEM image of an embodiment of a plurality of the golf ball microparticles of the present invention according to example 2.

Example 2 also referred to as HPbCD 100 shows microparticles are obtained by spray-drying of a liquid with a 10% HPBCD, a nozzle diameter of 0.4 mm, an inlat temperature of 140° C., a pump speed of 200 RPM and a nozzle gas pressure 4 bar. The SEM is shown in FIG. 12.

Comparative Examples 1 and 2

Figure 13:
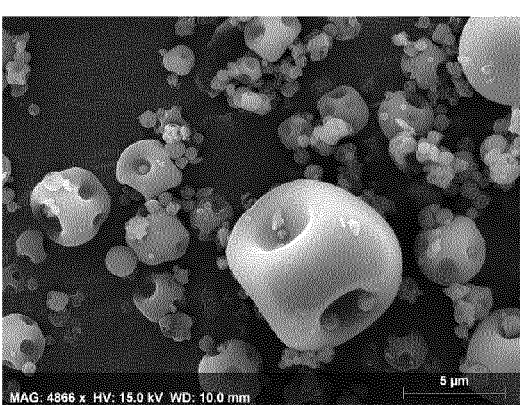
FIG. 13 is an SEM image of comparative example 1.

The less deflated balls of comparative example 1—also referred to as HPbCD AQ June 2020 2% —are obtained by spray-drying of a liquid with a 2% HPBCD, a nozzle diameter of 0.2 mm, an inlat temperature of 160° C., a pump speed of 200 RPM and a nozzle gas pressure of 4 bar. The SEM is shown in FIG. 13.

Figure 14:
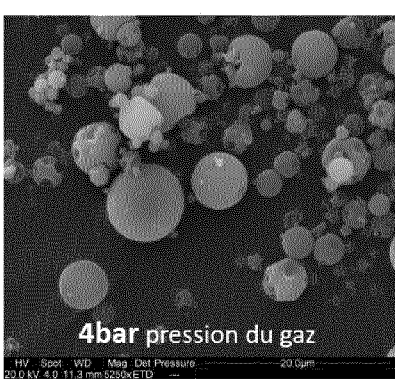
FIG. 14 is an SEM image of comparative example 2.

The less deflated balls of comparative example 2—also referred to as HPbCD AQ June 2020 5% —are obtained by spray-drying of a liquid with a 5% HPBCD, a nozzle diameter of 0.2 mm, an inlat temperature of 100° C., a pump speed of 200 RPM and a nozzle gas pressure of 4 bar. The SEM is shown in FIG. 14.

FIGS. 15 and 16 show the NGI deposition described below of three repetitions. The golf-ball-like particles of the invention perform better than Symbicort® on the one and side and less deflated balls on the other hand side. The deposition in the device (dispositive) is higher with Symbicort. The deposition in the deep lung (stages 2, 3, 4, 5) are better by the golf-ball like microparticles of the invention according to examples 1 and 1 as compared to the less deflated balls of comparative examples 1 and 2.

FIG. 17 shows the Fine Particle Fraction (FPF) of the budesonide and formoterol of examples 1 and 2 and comparative examples 1 and 2 as well as Symbicort.

Examples 3 and 4 and Comparative Examples 3 and 4

Active pharmaceutical ingredients were budesonide and formoterol with varying levels of the carrier hydroxypropyl-beta-cyclodextrin of 2, 5 and 10 w % of the solid content and varying spray-drying conditions as to nozzle size, temperature and pressure.

Chemicals and Solutions

HPBCD (Kleptose HPB–molar substitution=0.63) was provided by Roquette (Lestrem, France). Budesonide Ph.

Eur. 8.3 Micronized was obtained from Crystal Pharma and Formoterol Fumarate dehydrate Micronized from CHEMO Industriale chimica.

Budesonide and Formoterol Quantification

High performance liquid chromatography (HPLC) was used to quantify budesonide and formoterol using a HPLC Agilent série 1100, UV detector operating at 243 nm and with a 3*50 mm column filled 3.5 μm C18 (X Bridge BEH C18). The mobile phase was composed of Acetate ammonium buffer pH10/methanol at this gradient mode (0 min—55/45 (v/v), 1 min—55/45 (v/v); 2 min—35/65 (v/v); 7 min—35/65 (v/v); 8 min—55/45 (v/v); 20 min—55/45 (v/v)) at a flow rate of 0.7 ml/min. The column is heated up at 30° C. and sampler at 10° C.

The process was fully validated based on total error as decision criterion. The acceptance limits were set at 10%. All validation results were computed using the e-novall software (Arlenda, Liege, Belgium).

HPBCD-Budesonide-Formoterol Solution

Before atomization, the solutions containing the two active ingredients budesonide and formoterol are prepared as follows. Concentration of HPBCD were 2, 5 or 10% (g/100 ml). The excipients (99.29 w %) are first weighed and diluted in miQ water. After complete dissolution, this solution is divided in half and placed on a heating stirring bath (37° C.). The active ingredients (0.71 w %) are added separately in one of the two excipient solutions and dissolved under magnetic stirring at 37° C. for 2 hours. Budesonide is present at 97% and formoterol at 3% in the solution. After complete dissolution, the two solutions are combined before atomization.

Spray-Drying

A procept 4M8-Trix Formatrix spray-dryer (Procept, Zelzate, Belgium) with bi-fluid nozzle was used. Four different powders were produced from different solutions and different process parameters:

TABLE 1*

| Process parameters production | | | | |
| --- | --- | --- | --- | --- |
| | AQU | HPd3 2% | HPd3 5% | JT OPT |
| Solid content (w/w) % | 5 | 2 | 5 | 10 |
| Cyclone Gas Pressure (bar) | 0.75 | 0.75 | 0.75 | 0.75 |
| Inlet Gas Flow (q $^{7S}$/min) | 0.4 | 0.4 | 0.4 | 0.4 |
| Inlet T° (° C.) | 140 | 100 | 100 | 160 |
| Pump Speed (RPM) | 200 | 200 | 200 | 100 |
| Nozzle Gas Pressure (bar) | 4 | 4 | 4 | 2.25 |
| Nozzle diameter (mm) | 0.4 | 0.2 | 0.2 | 0.6 |

Particle Size Distribution Measurement

A laser diffractometer Mastersizer 2000 connected with a Scirocco powder feeder Malvem, UK) was used to estimate the inhalable fraction (1-5 mm) of powders produced during the design of experiment. A dispersion pressure of 4 bars and a measuring time of 10 s were used. For each sample, approximately 150 mg of powder was used to obtain the required obscuration of 0.5-5%.

Scanning Electron Microscopy

The particulate structure was observed by scanning electron microscopy (SEM) using either a Philips XL30 ESEM, or a FEI Quanta 600 after metallization with Au (~50 nm). Representative micrographs were captured, and a dozen particles were sampled for each powder to measure their diameter, and quantify their structure in terms of number and depth of the surface depressions also referred to as dimples.

Thermogravimetric Analysis

The residual moisture content of the samples was investigated directly after spray-drying by using a TGA 7 (Perkin Elmer, Norwalk, CT). Powder samples between 3 and 12 mg were loaded onto a platinum sample pan and heated from 25 to 150° C. at a rate of 10° C./min.

Bulk and Tapped Density

Bulk density and tapped density were obtained by following the Ph. Eur. procedure 2.9.34 [15]. Due to the small amount of sample, a 10-mL tarred graduated cylinder was used. The bulk volume used for the calculation of the bulk density was directly read from the cylinder.

Bulk density (g/ml)=(weight of powder)/(bulk powder volume)

The tapped density is obtained by mechanically tapping a graduated measuring cylinder containing the powder sample [15]. The tapped density is read after 1250 taps corresponding to 5 min at a tapping height of 3 mm. The mean value of three replicates is recorded along with the observed variances among the experiments.

Tapped density (g/ml)=(weight of powder)/(tapped powder volume)

The Carr index (%) is also calculated as followed= ((initial volume (ml)–final volume (ml))/final volume (ml))*100

The Hausner ratio is also calculated as followed=initial volume (ml)/final volume (ml)

In-Vitro Powder Aerosolisation

The pulmonary deposition profile of the powder produced during spray drying is determined in vitro by a New Generation Impactor (NGI). The device, a dry powder inhaler, is connected to the induction port by a mouthpiece mimicking the mouth. The NGI is divided into 8 stages characterized by a pore diameter covering a particle size range between 0.206 μm and 12.8 μm. A pump, connected to the NGI, allows the pressure and flow to be adjusted. Twelve capsules, containing a known mass of powder, are perforated by the device, of the Aerolizer® type, and emptied of their contents. This passes through the NGI at a flow rate of 100 mL/min for a period of 2.4 seconds. Once these twelve capsules have been introduced, the powder deposited at each level is recovered using a methanol/water solvent (65/35 V/V) and analyzed by HPLC. The total mass measured after each test in the throat and in stages 1 to 8 is defined as the recovered dose (RD). The fine particle dose (FPD) is defined as the total mass ranging from 0 μm to 5 μm. The fine particle fraction is calculated by dividing the FPD by the RD expressed as a percentage.

Results

Powder Characteristics

TABLE 2*

| Evaluation of powders properties | | | | |
| --- | --- | --- | --- | --- |
| Powder properties | AQU | HPd3 2% | HPd3 5% | JT OPT |
| Process yield (%) | 75.05 | 74 | 71.2 | 83.2 |
| Particle size (d0.5) | 2.57 | 1.79 | 3.65 | 2.15 |
| Carr index (%) | 68.1 | 50.9 | 62.5 | 36.9 |
| Water content (%) | 7.20 | 5.51 | 7.37 | 4.49 |

Powder Morphology

The morphology of all powders has been analyzed by SEM. Each powder has been scanned. We have chosen pictures which are the most representative of all powder population.

Powders have different morphology. While examples 3 and 4 also referred to as JT OPT and AQU powders more than 50 surface % of surface depressions or dimples, comparative examples 3 and 4 also referred to as HPd3 2% and HPd3 5% show fewer surface depressions. These differences are due to the different atomization process parameter.

The morphology of all powders has been analyzed by SEM. Each powder of example 3 and 4 and comparative examples 3 and 4 has been scanned. Representative SEM images are shown in FIGS. 18, 19 (examples 3 and 4) and comparative FIGS. 20, 21 (comparative examples 3 and 4).

TABLE 3*

| Evaluation of powders in terms of dimples number based on SEM pictures | | | | |
| --- | --- | --- | --- | --- |
| Powder properties | AQU | HPd3 2% | Pd3 5% | JT OPT |
| Dimples number | 10 | 6 | 8 | 13 |

Powders In Vitro Lungdeposition

FIGS. 22 and 23 show the evaluation of the powders according to examples 3 and 4 and comparative examples 3 and 4.

FIGS. 24 and 25 show the Fine Particles Fraction (FPF) obtained for the four powders according to examples 3 and 4 and comparative examples 3 and 4 using NGI apparatus. FPF was calculated compared to the total dose powder or compared to the Recovery Dose (RD=powder in throat, pre-separator and all stages) n=3.

CONCLUSIONS

Different solid content of spray dried solutions and different atomization process parameters according to examples 3 and 4 and comparative examples 3 and 4 produce HPβCD microparticle powders containing budesonide and formoterol with different morphologies.

Difference of lung deposition have been found between powders according to examples 3 and 4 and comparative examples 3 and 4. With similar particle size or water content, the morphological differences between the powders according to examples 3 and 4 and comparative examples 3 and 4 explain the different lung deposition performances.

Examples 13 to 27

Microparticles with the API Budesonide (BD)-Hydroxypropylbetacyclodextrin (HPBCD) and cyclodextrins were 15 obtained through spray-drying. Budenoside was used in the amount of 106 μg in 15 mg of spray-dried powder. Following combinations were tested:

Budesonide-HPBCD (test14)
Budesonide-HPBCD+5% L-leucine (test 15)
Budesonide-HPBCD+10% L-leucine (test 13) 20
Budesonide-Formoterol-HPBCD powder with 106 μg of Budesonide and 3 μg of formoterol in 15 mg of powder:
Budesonide-Formoterol-HPBCD (test 16)
Budesonide-Formoterol-HPBCD+5% L-leucine (test 19)
25

Comparative Example: Miflonide® (Novartis)
Containing 230 μg of Budesonide

Tested formulations and their particle size distribution are shown in table 1. The spray-drying parameters are shown in Table 2.

The golf-ball like microparticles of Table 1 spray-dried according to the process conditions shown in Table 2 were then evaluated for their aerodynamic properties using Next Generation Impactor (NGI) as recommended by European Pharmacopeia and USP, the results of which are shown in Tables 4 to 6. Aerolizer® was used for 5 testing. HPLC standard reagents Methanol and Milli-Q water were used.

The NGI was assembled and a pre-separator was used for Miflonide since the formulation contains lactose. By means of the regulator and a flow meter connected to the inlet nozzle, the flow rate was adjusted to provide a steady state of 100 L/min plus, minus 5% in the apparatus. 10 The air circulation was stopped. The nozzle adapter at the end of the intake nozzle was installed. A certain number of doses was released from the inhaler according to the directions for use:

For Budesonide-HPBCD and Budesonide-Formoterol-HPBCD (15 mg of powders): 10 doses 15

Miflonide 230 μg of budesonide: 5 doses

Then the pump was turned on the solenoid valve was closed, and the inhaler was placed in the adapter. A discharge of powder was let into the device by opening the solenoid valve for 2.4 seconds (4 L of 20 air). The capsule was put inside a flask. The volumes are described in Table 3 below.

The inhaler and mouthpiece adapter were removed from the NGI Induction Port. The active ingredient was extracted from the inhaler 25 and mouthpiece in the same flask (see volume in Table 3 below) with the mix methanol/water 65/35.

The active ingredients from the induction port were extracted in a flask with the mix methanol/water 65/35. For Miflonide, the active ingredients were extracted from the pre-separator in a flask. The volumes are indicated in Table 3A below.

Then, the NGI was opened and the contents retrieved in the eight collection cups:

10 mL of mix methanol/water 65/35 were added in 5 each cup and mix it shaking gently each cup until complete dissolution. Each solution was put in different flasks (see volume in Table 3A below).

the "backside" of each nozzle piece was extracted by placing the seal body vertically with the help of two supports.

the nozzles of stages 1 through 8 were rinsed using 1010 mL of the mix methanol/water 65/35 and the solution was put in the corresponding flask and was filled up to the mark with the mix. After mixing and sonication for 15 minutes the solution was analyzed in HPLC.

Fine Particle Dose (FPD), MMAD and GSD were calculated by the software CITDAS (Copley). Fine Particle Fraction (FPF) which is the 15 percentage of FPD over the nominal dose, is calculated manually.

It should be understood that the present invention is not limited to the described embodiments and that variations can be applied without going outside of the scope of the appended claims.

TABLE 1

| | | | | | | Solid | | | | | % Frac |
| | | % | % | % | % | content | D10 | D50 | D90 | | <5 μm |
| Example | Formulation | Bodesonide | Formoterol | Leucine | HPBCD | (% w/w) | (μm) | (μm) | (μm) | SPAN | (%) |
|---|---|---|---|---|---|---|---|---|---|---|---|
| 13 | Budesonide-HPBCU-10% Leucine | 0.01 | 0.00 | 0.10 | 0.89 | 0.05 | 0.53 | 2.29 | 5.06 | 1.98 | 89.67 |
| 14 | Budesonide-HPBCD | 0.01 | 0.00 | 0.00 | 0.99 | 0.05 | 0.56 | 2.28 | 5.11 | 1.99 | 89.40 |
| 15 | Budesonide-HPBCD-5% Leucine | 0.01 | 0.00 | 0.05 | 0.94 | 0.05 | 0.53 | 2.16 | 4.83 | 1.99 | 91.45 |
| 16&17 | Budesonide-HPBCD-Formoterol | 0.01 | 0.00 | 0.00 | 0.99 | 0.05 | 0.58 | 2.37 | 5.04 | 1.88 | 89.76 |
| 19 | HPBCD-0.0040% Formoterol | 0.01 | 0.00 | 0.05 | 0.94 | 0.05 | 0.54 | 2.29 | 5.05 | 1.97 | 89.75 |
| 20 | Budesonide-HPBCD | 0.01 | 0.00 | 0.00 | 0.99 | 0.05 | 0.57 | 2.32 | 5.23 | 2.01 | 88.70 |
| 21 | Budesonide-HPBCD-5% Leucine | 0.01 | 0.00 | 0.05 | 0.94 | 0.05 | 0.60 | 2.52 | 5.44 | 1.92 | 87.08 |
| 22 | Budesonide-HPBCD-1% Leucine | 0.00 | 0.01 | 0.01 | 0.99 | 0.05 | 0.59 | 2.44 | 5.42 | 1.98 | 87.23 |
| 24 | Budesonide-Formoterol-HPBCD-2% Leucine | 0.01 | 0.00 | 0.02 | 0.97 | 0.05 | 0.61 | 2.40 | 5.36 | 1.98 | 87.89 |
| 25 | Budesonide-HPBCD-2% Leucine | 0.01 | 0.00 | 0.02 | 0.97 | 0.05 | 0.58 | 2.39 | 5.41 | 2.02 | 87.59 |
| 26 | Budesonide-HPBCD | 0.01 | 0.00 | 0.00 | 0.99 | 0.05 | 0.58 | 2.19 | 4.82 | 1.94 | 91.47 |
| 27 | Budesonide-HPBCD-5% Leucine | 0.01 | 0.00 | 0.05 | 0.94 | 0.05 | 0.53 | 2.16 | 4.85 | 1.99 | 91.23 |

Formulations and particle size distribution

US 12,558,313 B2

17 18

TABLE 2

| Spray drying conditions of the examples of Table 1 | | | | | | | | | | |
|---|---|---|---|---|---|---|---|---|---|---|
| Example | 13 | 14 | 15 | 16 | 17 | 18 | 19 | 20 | 21 | 22 |
| API | BD | BD | BD | BD | BD | BD | BD Form | BD | BD | BD |
| complex | HPBCD | HPBCD | HPBCD | HPBCD | HPBCD | HPBCD | HPBCD | HPBCD | HPBCD | HPBCD |
| Leucine | 10% | / | 5% | / | / | / | 5% | / | 5% | 1% |
| Solvent | Water | Water | Water | Water | Water | Water | Water | Water | Water | Water |
| Solid content | 5.00% | 5.00% | 5.00% | 5.00% | 5.00% | 5.00% | 5.00% | 5.00% | 5.00% | 5.00% |
| Temp (° C.) | 120 | 120 | 120 | 120 | 126 | 126 | 128 | 140 | 140 | 140 |
| Temp chamber out (° C.) | 57 | 57 | 57 | 56 | 52 | 53 | 53 | 57 | 57 | 57 |
| Temp before cyclone (° C.) | 44 | 44 | 44 | 43 | 43 | 42 | 44 | 52 | 52 | 51 |
| Cyclone | Small | Small | Small | Small | Small | Small | Small | Small | Small | Small |
| Pressure drop cyclone (mbar) | 82 | 82 | 82 | 82 | 82 | 82 | 82 | 82 | 82 | 84 |
| Airflow (m²/min) | 0.3 | 0.3 | 0.3 | 0.3 | 0.3 | 0.3 | 0.3 | 0.4 | 0.4 | 0.4 |
| Cooling air (l/min) | 146 | 146 | 146 | 146 | 146 | 146 | 146 | 0 | 0 | 0 |
| Bi-fluid Nozzle (mm) | 0.4 | 0.4 | 9.4 | 0.4 | 0.4 | 0.4 | 0.4 | 0.4 | 0.4 | 0.4 |
| Nozzle Air | 14 | 14 | 14 | 14 | 14 | 14 | 14 | 20 | 20 | 20 |
| US Nozzle (kHz) | / | / | / | / | / | / | / | / | / | / |
| Amplitude (Watt) | / | / | / | / | / | / | / | / | / | / |
| Spray rate (g/min) | 4.7 | 4.7 | 4.7 | 4.7 | 4.7 | 4.7 | 4.7 | 10 | 10 | 10 |
| Pumping speed (rpm) | 66 | 66 | 86 | 66 | 66 | 66 | 66 | 160 | 160 | 160 |
| Tube type (ID) resistant | 1.2 | 1.2 | 1.2 | 1.2 | 1.2 | 1.2 | 1.2 | 1.2 | 1.2 | 1.2 |
| Total dosed sample (g) | 200 | 97.70 | 99.90 | 50.00 | 547.00 | 497.00 | 99.00 | 1399.60 | 1396.00 | 923.40 |
| Recovered solid (g) | 8.45 | 4.33 | 4.09 | 1.83 | 23.45 | 21.56 | 4.42 | 65.47 | 63.67 | 42.12 |
| Total solid dosed (g) | 10 | 4.89 | 5.00 | 2.50 | 27.35 | 24.85 | 4.95 | 69.98 | 69.80 | 46.17 |
| Recovery (%) | 84.5 | 89 | 82 | 73 | 86 | 87 | 89 | 94 | 91 | 91 |

| Example | 24 | 25 | 26 | 27 |
|---|---|---|---|---|
| API | Bud Form | BD | BD | BD |
| complex | HPBCD | HPBCD | HPBCD | HPBCD |
| Leucine | 2% | 2% | 0% | 5% |
| Solvent | Water | Water | Water | Water |
| Solid content | 5.45% | 5.00% | 5.00% | 5.00% |
| Temp (° C.) | 140 | 140 | 140 | 140 |
| Temp chamber out (° C.) | 56 | 54 | 57 | 56 |
| Temp before cyclone (° C.) | 54 | 53 | 55 | 54 |
| Cyclone | Small | Small | Small | Small |
| Pressure drop cyclone (mbar) | 84 | 84 | 84 | 84 |
| Airflow (m²/min) | 0.4 | 0.4 | 0.4 | 0.4 |
| Cooling air (l/min) | 0 | 0 | 0 | 0 |
| Bi-fluid Nozzle (mm) | 0.4 | 0.4 | 0.4 | 0.4 |
| Nozzle Air | 20 | 20 | 20 | 20 |
| US Nozzle (kHz) | / | / | / | / |
| Amplitude (Watt) | / | / | / | / |
| Spray rate (g/min) | 10 | 10 | 10 | 10 |
| Pumping speed (rpm) | 160 | 160 | 160 | 160 |
| Tube type (ID) resistant | 1.2 | 1.2 | 1.2 | 1.2 |
| Total dosed sample (g) | 1092.00 | 1196.30 | 1204.00 | 1206.00 |
| Recovered solid (g) | 52.83 | 52.55 | 55.09 | 54.22 |
| Total solid dosed (g) | 59.61 | 59.82 | 57.60 | 60.30 |
| Recovery (%) | 89 | 88 | 96 | 90 |

TABLE 3A

| Volumes of flask to use for each extraction | | |
|---|---|---|
| | Budesonide-HPBCD or Budesonide-Formoterol-HPBCD | Miflonide |
| Capsules/Device/Mouthpiece | 50 mL | 50 mL |
| Induction port | 50 mL | 50 mL |
| Pre-separator | — | 100 mL |
| Stage 1 | 25 mL | 25 mL |
| Stage 2 | 25 mL | 25 mL |
| Stage 3 | 25 mL | 25 mL |
| Stage 4 | 25 mL | 25 mL |
| Stage 5 | 25 mL | 25 mL |

TABLE 3A-continued

| Volumes of flask to use for each extraction | | |
|---|---|---|
| | Budesonide-HPBCD or Budesonide-Formoterol-HPBCD | Miflonide |
| Stage 6 | 25 mL | 25 mL |
| Stage 7 | (grouped | (grouped |
| Stage 8 | together) | together) |

TABLE 3B

Effective cut-off diameter (ECD) at 100 L/min or each stage is given in the table below:

| ECD (μm) at 100 L/min | Mass of budesonide deposited per discharge (μg) | Cumulated mass of budesonide deposited per discharge(mg) | Cumulative percentage (%) |
|---|---|---|---|
| $d_7 = 0.24$ | mass extracted at stage 8, $m_8$ | $c_7 = m_8$ | $f_7 = (c_7/c) \cdot 100$ |
| $d_6 = 0.40$ | mass extracted at stage 7, $m_7$ | $c_6 = c_7 + m_7$ | $f_6 = (c_6/c) \cdot 100$ |
| $d_5 = 0.72$ | mass extracted at stage 6, $m_6$ | $c_5 = c_6 + m_6$ | $f_5 = (c_5/c) \cdot 100$ |
| $d_4 = 1.31$ | mass extracted at stage 5, $m_5$ | $c_4 = c_5 + m_5$ | $f_4 = (c_4/c) \cdot 100$ |
| $d_3 = 2.18$ | mass extracted at stage 4, $m_4$ | $c_3 = c_4 + m_4$ | $f_3 = (c_3/c) \cdot 100$ |

TABLE 3B-continued

Effective cut-off diameter (ECD) at 100 L/min or each stage is given in the table below:

| ECD (μm) at 100 L/min | Mass of budesonide deposited per discharge (μg) | Cumulated mass of budesonide deposited per discharge(mg) | Cumulative percentage (%) |
|---|---|---|---|
| $d_2 = 3.42$ | mass extracted at stage 3, $m_3$ | $c_2 = c_3 + m_3$ | $f_2 = (c_2/c) \cdot 100$ |
| $d_1 = 6.17$ | mass extracted at stage 2, $m_2$ | $c_1 = c_2 + m_2$ | $f_1 = (c_1/c) \cdot 100$ |
|  | mass extracted at stage 1, inhalator, mouthpiece and induction port, m | $c = c_1 + m$ | 100 |

TABLE 4

Comparative example and exemplary embodiments of the invention and their NGI deposition

| | Comparative example Miflonide | | | Budesonide-HPBCD (example 14) | | | Budesonide-HPBCD (example 20) | | |
|---|---|---|---|---|---|---|---|---|---|
| Average % Budesonide | | | | | | | | | |
| | NA | | | NA | | | 0.64 | | |
| μg Budesonide | | | | | | | | | |
| | 230.00 | 230.00 | | 106.00 | 106.00 | | 96.69 | 96.31 | |
| Total dose (μg) | | | | | | | | | |
| | 1150.00 | 1150.00 | | 1060.00 | 1060.00 | | 966.89 | 963.14 | |
| | NGI 1 in μg | NGI 2 in μg | Average in μg | NGI 1 in μg | NGI 2 in μg | Average in μg | NGI 1 in μg | NGI 2 in μg | Average in μg |
| Capsule/device/mouthpiece | 256.60 | 277.80 | 267.20 | 97.75 | 51.30 | 74.53 | 191.15 | 173.60 | 182.38 |
| Induction port | 138.15 | 161.10 | 149.63 | 93.95 | 108.80 | 101.38 | 72.35 | 82.25 | 77.30 |
| Pre-separator | 476.65 | 524.00 | 500.33 | | | | | | |
| Stage 1 | 19.48 | 26.48 | 22.98 | 51.00 | 48.35 | 49.68 | 60.43 | 57.18 | 58.80 |
| Stage 2 | 29.20 | 47.85 | 38.53 | 139.53 | 135.83 | 137.68 | 138.08 | 144.10 | 141.09 |
| Stage 3 | 42.78 | 68.53 | 55.65 | 147.33 | 131.28 | 139.30 | 147.03 | 158.85 | 152.94 |
| Stage 4 | 50.30 | 71.38 | 60.84 | 110.83 | 111.33 | 111.08 | 104.18 | 112.28 | 108.23 |
| Stage 5 | 23.63 | 26.20 | 24.91 | 79.15 | 87.25 | 83.20 | 57.90 | 56.90 | 57.40 |
| Stage 6, 7, 8 | 14.03 | 16.65 | 15.34 | 92.15 | 99.48 | 95.81 | 73.18 | 69.73 | 71.45 |
| Recovery (%) | 91.37 | 106.08 | 98.73 | 76.57 | 72.98 | 74.78 | 87.32 | 88.76 | 88.04 |
| MMAD (μm) | 3.08 | 3.33 | 3.21 | 2.37 | 2.25 | 2.31 | 2.58 | 2.59 | 2.58 |
| GSD | 2.26 | 2.10 | 2.18 | 2.00 | 2.08 | 2.04 | 1.99 | 1.93 | 1.96 |
| FPD (<5.0 μm) (μg) | 26.63 | 37.33 | 31.98 | 53.35 | 53.09 | 53.22 | 48.34 | 50.42 | 49.38 |
| FPF (<5.0 μm) (%) | 11.58 | 16.23 | 13.90 | 50.33 | 50.08 | 50.21 | 50.00 | 52.35 | 51.17 |
| FPF over recovered dose (%) | 25.34 | 30.60 | 28.17 | 65.73 | 68.63 | 67.14 | 57.26 | 58.98 | 58.12 |

TABLE 5

Further exemplary embodiments of the invention and their NGI deposition

|  | Budesonide-HPBCD (example 26) | | | Budesonide-HPBCD + 10% Leucine (example 13) | | | Budesonide-HPBCD + 5% Leucine (example 15) | | |
|---|---|---|---|---|---|---|---|---|---|
| Average % Budesonide | 0.66 | | | NA | | | NA | | |
| μg Budesonide | 99.81 | 100.55 | | 106.00 | 106.00 | | 106.00 | 106.00 | |
| Total dose (μg) | 998.13 | 1005.47 | | 1060.00 | 1060.00 | | 1060.00 | 1060.00 | |
|  | NGI 1 in μg | NGI 2 in μg | Average in μg | NGI 1 in μg | NGI 2 in μg | Average in μg | NGI 1 in μg | NGI 2 in μg | Average in μg |
| Capsule/device/mouthpiece | 138.35 | 142.10 | 140.23 | 59.30 | 53.58 | 56.58 | 66.60 | 56.95 | 61.78 |
| Induction port | 86.85 | 105.90 | 96.38 | 124.10 | 103.25 | 113.68 | 88.25 | 82.20 | 85.23 |
| Pre-separator |  |  |  |  |  |  |  |  |  |
| Stage 1 | 50.05 | 66.15 | 58.10 | 54.28 | 49.20 | 51.74 | 41.03 | 39.70 | 40.36 |
| Stage 2 | 154.50 | 152.15 | 153.33 | 141.65 | 139.00 | 140.33 | 133.23 | 115.53 | 124.88 |
| Stage 3 | 144.30 | 143.80 | 144.05 | 128.45 | 114.08 | 121.26 | 123.03 | 102.35 | 112.69 |
| Stage 4 | 90.15 | 98.88 | 94.51 | 86.33 | 83.50 | 84.91 | 116.08 | 97.15 | 106.61 |
| Stage 5 | 74.10 | 76.60 | 75.35 | 69.83 | 61.73 | 65.78 | 92.68 | 82.73 | 87.70 |
| Stage 6, 7, 8 | 99.20 | 87.98 | 93.59 | 93.55 | 112.23 | 102.89 | 109.35 | 126.85 | 118.10 |
| Recovery (%) | 83.91 | 86.88 | 85.39 | 71.46 | 67.63 | 69.54 | 72.66 | 66.46 | 69.56 |
| MMAD (μm) | 2.49 | 2.54 | 2.52 | 2.48 | 2.38 | 2.43 | 2.09 | 1.93 | 2.01 |
| GSD | 1.94 | 2.03 | 1.99 | 2.01 | 2.06 | 2.04 | 2.14 | 2.32 | 2.23 |
| FPD (<5.0 μm) (μg) | 52.36 | 51.86 | 52.11 | 48.30 | 47.51 | 47.90 | 54.21 | 49.68 | 51.94 |
| FPF (<5.0 μm) (%) | 52.46 | 51.58 | 52.02 | 45.56 | 44.82 | 45.19 | 51.14 | 46.87 | 49.00 |
| FPF over recovered dose (%) | 62.52 | 59.37 | 60.91 | 63.76 | 66.27 | 67.98 | 70.38 | 70.52 | 70.45 |

TABLE 6

Further exemplary embodiments of the invention and their NGI deposition

|  | Budesonide-HPBCD +5% Leucine (example 21) | | | Budesonide-HPBCD + 5% Leucine (example 27) | | | Budesonide-HPBCD + 2% Leucine (example 25) | | | Budesonide-HPBCD + 1% Leucine (example 22) | | |
|---|---|---|---|---|---|---|---|---|---|---|---|---|
| Average % Budesonide | 0.64 | | | 0.65 | | | 0.67 | | | 0.66 | | |
| μg Budesonide | 96.16 | 96.10 | | 99.49 | 100.28 | | 99.96 | 100.45 | | 102.18 | 100.34 | |
| Total dose (μg) | 961.60 | 961.03 | | 994.93 | 1002.78 | | 999.63 | 1004.49 | | 1021.84 | 1003.40 | |
|  | NGI 1 in μg | NGI 2 in μg | Average in μg | NGI 1 in μg | NGI 2 in μg | Average in μg | NGI 1 in μg | NGI 2 in μg | Average in μg | NGI 1 in μg | NGI 2 in μg | Average in μg |
| Capsule/device/mouthpiece | 168.65 | 154.60 | 161.63 | 125.45 | 136.50 | 130.98 | 136.10 | 156.20 | 146.15 | 160.55 | 169.25 | 164.90 |
| Induction port | 80.20 | 81.90 | 81.05 | 131.85 | 76.25 | 104.05 | 65.70 | 88.40 | 77.05 | 70.95 | 74.95 | 72.95 |
| Pre-separator |  |  |  |  |  |  |  |  |  |  |  |  |
| Stage 1 | 58.05 | 64.63 | 61.34 | 70.70 | 62.10 | 66.40 | 70.95 | 61.18 | 60.06 | 85.46 | 70.63 | 78.04 |
| Stage 2 | 164.90 | 158.53 | 161.71 | 140.73 | 143.45 | 142.09 | 163.53 | 154.88 | 159.20 | 154.53 | 145.65 | 150.09 |
| Stage 3 | 146.75 | 144.83 | 145.79 | 121.68 | 129.93 | 125.80 | 130.18 | 119.78 | 124.98 | 129.80 | 128.58 | 129.19 |
| Stage 4 | 85.15 | 79.95 | 82.55 | 97.43 | 92.15 | 94.79 | 80.05 | 86.28 | 83.16 | 83.50 | 74.58 | 79.04 |
| Stage 5 | 53.13 | 55.63 | 54.38 | 75.85 | 77.65 | 76.75 | 71.25 | 72.00 | 71.63 | 68.68 | 65.88 | 67.28 |
| Stage 6, 7, 8 | 77.93 | 74.38 | 76.15 | 77.85 | 104.40 | 91.13 | 112.38 | 89.20 | 100.79 | 92.73 | 95.98 | 94.35 |
| Recovery (%) | 86.81 | 84.75 | 85.78 | 84.58 | 82.01 | 83.30 | 83.04 | 82.42 | 82.73 | 82.81 | 82.27 | 82.54 |
| MMAD (μm) | 2.76 | 2.79 | 2.78 | 2.54 | 2.42 | 2.48 | 2.60 | 2.57 | 2.59 | 2.71 | 6.64 | 2.67 |
| GSD | 1.87 | 1.91 | 1.89 | 2.14 | 2.10 | 2.12 | 2.05 | 2.03 | 2.04 | 2.12 | 2.07 | 2.10 |
| FPD (<5.0 μm) (μg) | 48.51 | 47.08 | 47.80 | 47.46 | 50.94 | 49.20 | 51.32 | 48.12 | 49.72 | 48.54 | 47.05 | 47.79 |
| FPF (<5.0 μm) (%) | 50.45 | 48.99 | 49.72 | 47.71 | 50.80 | 49.25 | 51.34 | 47.90 | 49.62 | 47.50 | 46.89 | 47.20 |
| FPF over recovered dose (%) | 58.11 | 57.81 | 57.96 | 56.40 | 61.94 | 59.14 | 61.83 | 58.12 | 59.97 | 57.36 | 57.00 | 57.18 |

The invention claimed is:

1. A plurality of spherical or non-spherical microparticles obtained by spray-drying a nanosuspension or solution of a mix of one or more carriers, said carrier comprising at least one of cyclodextrin, one or more active pharmaceutical ingredients and a polar solvent, wherein the cyclodextrin is present in an amount of 80% or more compared to a total weight of the microparticle, for use in the treatment of respiratory diseases, the spherical or non-spherical microparticles comprising one or more cyclodextrin carriers and one or more active pharmaceutical ingredients, wherein a. the microparticles have a median mass aerodynamic diameter of 0.1 microns or more and 5 microns or less;

b. the microparticles have a plurality of golf ball-like surface depressions identifiable by scanning electron microscopy;

c. the average maximum depth d of the surface depressions (1) is between 5% or more and 30% or less of a diameter of the microparticles as compared to the average maximum diameter D of the microparticles; and d. 50% or more of a surface area of the microparticles as compared to the total surface of the microparticles are depressed;

e. the average number of surface depressions per microparticle is 10 or more, and f. the Fine Particle Fraction of the plurality of microparticles is 50% or more.

2. The microparticles of claim 1 wherein the average maximal depth d of the surface depressions (1) is 25% or less as compared to the maximum diameter of the microparticle.

3. The microparticles of claim 1, wherein the average maximal depth d of the surface depressions (1) is 10% or more as compared to the maximum diameter D of the microparticle.

4. The microparticles of claim 1, wherein 70% or more of a surface area as compared to the total surface area of the microparticles are depressed.

5. The microparticles of claim 1, wherein the cyclodextrin of the carrier is chosen from the group consisting of alpha-cyclodextrin, beta-cyclodextrin, gamma-cyclodextrin, 2-hydroxypropyl-beta-cyclodextrin (HPBCD), 2-hydroxypropyl-gamma-cyclodextrin (HPGCD), sulfobutylether-beta-cyclodextrin, (SBEBCD), and methyl-beta-cyclodextrin (MBCD).

6. The microparticles of claim 1, wherein the cyclodextrin of the carrier is 2-hydroxypropyl-beta-cyclodextrin.

7. The microparticles of claim 1, wherein the cyclodextrin is present in an amount of 90 w. % or more as compared to the total weight of the microparticle.

8. The microparticles of claim 1, wherein the one or more active pharmaceutical ingredients are selected from the group consisting of corticosteroids, bronchodilators, antibiotics or anti-inflammatory compounds or combinations thereof.

9. The microparticles of claim 1, wherein the one or more active pharmaceutical ingredient is budesonide or formoterol or a combination thereof.

10. The microparticles of claim 1, further comprising amino acids.

11. A method of treatment of a disease comprising administering the of claim 1, wherein the microparticles are administered per inhalation in an amount effective to reduce, stabilize or positively impact the symptoms of the disease without causing treatment limiting side effects as compared to subjects untreated with the microparticles of the invention.

12. Process for the manufacturing of microparticles of claim 1, comprising the steps of:

a. mixing a carrier comprising at least a cyclodextrin, one or more active pharmaceutical ingredients, and a polar solvent to obtain a nanosuspension or a solution, and b. spray-drying of nanosuspension or solution of step a.

13. A method of treatment of a disease according to claim 11, wherein the side effects are selected from the group consisting of renal clearance, hepatic impairment as expressed by elevated levels of transaminase, and wheezing after administration.

14. A method of treatment of a disease according to claim 11, wherein the disease is a respiratory disease selected from the group consisting of asthma, chronic obstructive pulmonary disease (COPD), pulmonary fibrosis, pneumonia, and lung cancers.

15. The microparticles of claim 1, wherein the carrier further comprises leucine.

16. The microparticles of claim 1, wherein the one or more active pharmaceutical ingredients is selected from the group consisting of corticosteroids, bronchodilators, antibiotics or anti-inflammatory compounds or combinations thereof.

* * * * *